United States Patent [19]

Inaba et al.

[11] Patent Number: 4,995,396
[45] Date of Patent: Feb. 26, 1991

[54] RADIOACTIVE RAY DETECTING ENDOSCOPE

[75] Inventors: Makoto Inaba; Masaaki Hayashi, both of Hachioji; Toshihiko Hashiguchi, Sagamihara; Hiroki Hibino, Hachioji; Hiroyuki Sasa, Tokyo, all of Japan; David E. Barlow, Hicksville, N.Y.; Yutaka Ohshima, Hachioji, Japan; Kohichiro Ishihara, Hachioji, Japan; Yutaka Yanagawa, Hachioji, Japan; Motoyuki Tagawa, Hachioji, Japan; Shuichi Takayama, Hachioji, Japan; Takashi Tsukaya, Hachioji, Japan; Frank Klosterman, Hicksville; Jack Goodman, Huntington, both of N.Y.

[73] Assignee: Olympus Optical Co., Ltd., Tokyo, Japan

[21] Appl. No.: 281,426

[22] Filed: Dec. 8, 1988

[51] Int. Cl.$^5$ ............................. A61B 1/00; A61B 1/06
[52] U.S. Cl. ......................................... 128/654; 128/5; 128/6; 128/660.07; 128/662.03; 128/662.06; 358/98
[58] Field of Search ..................... 128/4, 6, 24 A, 654, 128/656, 657, 658, 660.01, 660.07, 662.03, 662.06; 358/98

[56] References Cited

U.S. PATENT DOCUMENTS

| | | |
|---|---|---|
| 3,665,916 | 5/1972 | Kobayashi et al. . |
| 3,669,095 | 6/1972 | Kobayashi et al. . |
| 3,670,719 | 6/1972 | Kobayashi et al. . |
| 4,595,014 | 6/1986 | Barrett et al. . |

FOREIGN PATENT DOCUMENTS

| | | |
|---|---|---|
| 40518 | 12/1970 | Japan . |
| 5168 | 2/1972 | Japan . |
| 4526 | 2/1973 | Japan . |

Primary Examiner—Max Hindenburg
Assistant Examiner—Krista M. Pfaffle
Attorney, Agent, or Firm—Armstrong, Nikaido, Marmelstein, Kubovcik & Murray

[57] ABSTRACT

A radioactive ray detecting endoscope comprises an elongated insertable part, an ultrasonic imaging apparatus provided in the tip part of the insertable part for transmitting ultrasonic waves toward an observed part, for receiving echoes from the observed part by these ultrasonic waves, and for outputting a signal for forming an ultrasonic image and a radioactive ray detecting apparatus arrangeable in the tip part of the insertable part for detecting radioactive rays. Preferably, the observing direction of the ultrasonic imaging apparatus and the detecting direction of the radioactive ray detecting apparatus substantially coincide with each other.

25 Claims, 25 Drawing Sheets

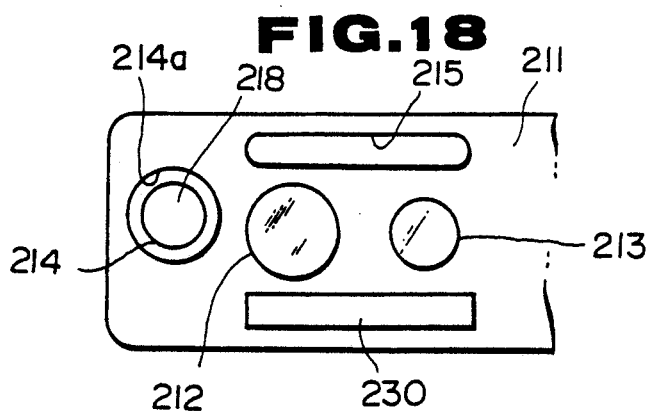
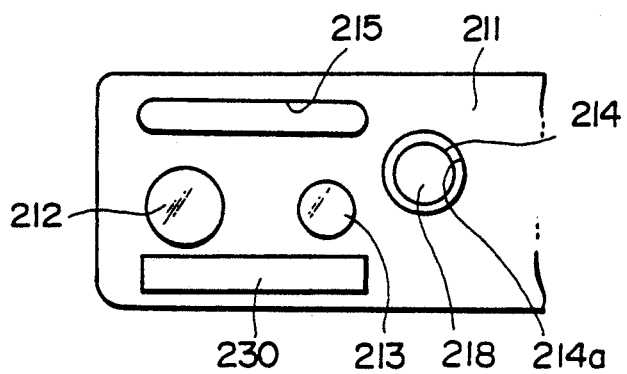
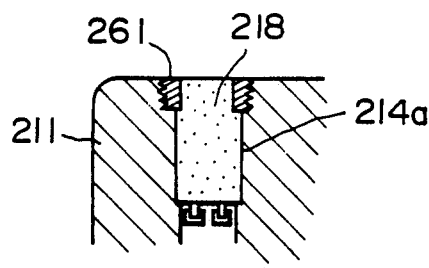
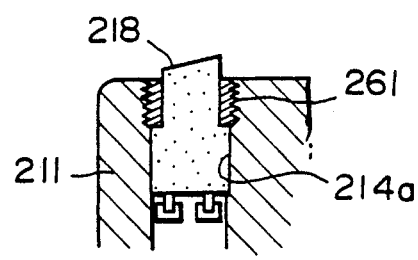
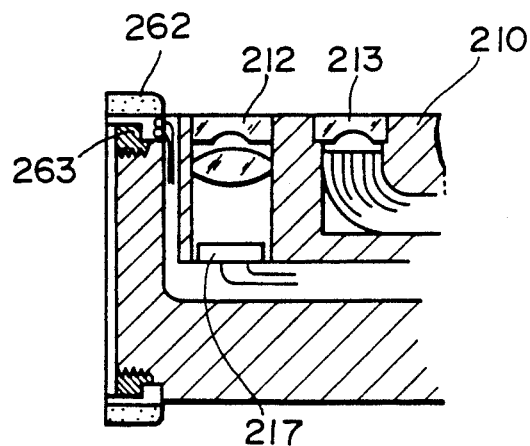

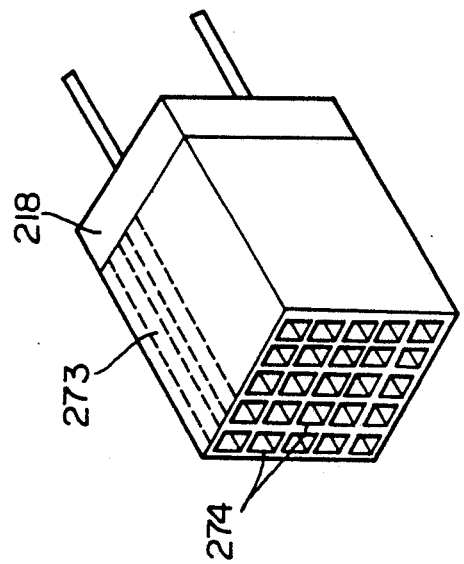
FIG. 28
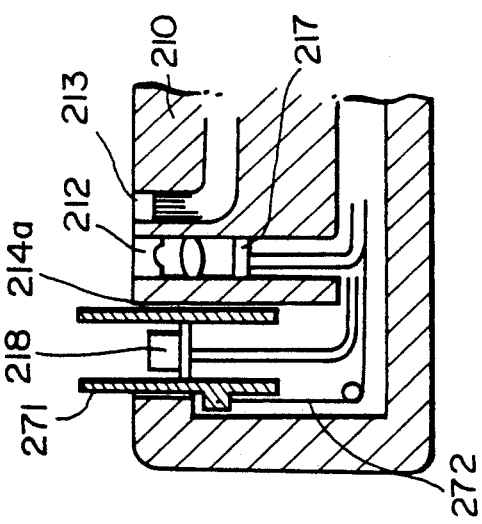
FIG. 27
FIG. 29(A) FIG. 29(B) FIG. 29(C) FIG. 29(D)

FIG. 38
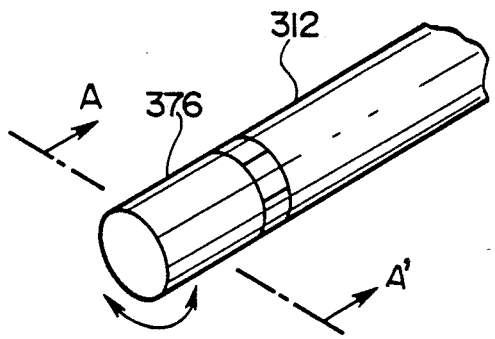
FIG. 39
FIG. 40(A)
FIG. 40(B)
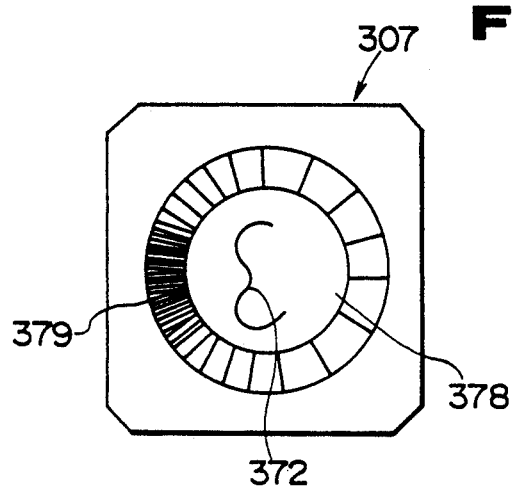
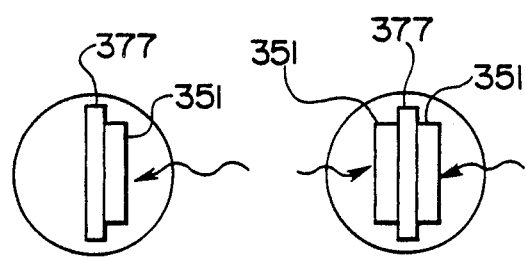
FIG. 41
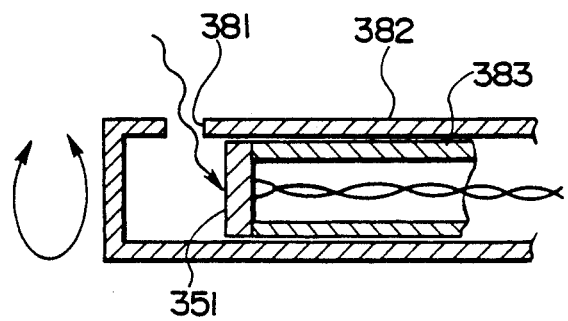

RADIOACTIVE RAY DETECTING ENDOSCOPE

BACKGROUND OF THE INVENTION

1. Field of the Invention:

This invention relates to an endoscope whereby radioactive rays can be detected.

2. Related Art Statement:

Recently, there is extensively utilized an endoscope whereby organs within a body cavity can be observed with an elongated insertable part inserted into a body cavity or, as required, various therapeutic treatments can be made by using a treating tool inserted through a treating tool channel.

The presence, penetrating range or transfer of a cancer is discovered by detecting radioactive rays emitted from cancer cells with a substance concentrating peculiarly on cancer cells and marked with a radioactive ray substance as a means of discovering and diagnosing a cancer.

Conventionally, a cancer has been detected and diagnosed to be present by leading into a body a sensor detecting such radioactive rays as $\beta$ rays by using a fiber scope as shown, for example, in Japanese utility model publication No. 5168/1972.

Also, a probe fitted with, for example, a semiconductor radioactive ray detector is disclosed in each of the publications of a Japanese utility model application publication No. 4526/1973, Japanese patent application publication Ser. No. 40518/1970 and U.S. Pat. Nos. 3,665,946, 3,339,095 and 4,595,014.

However, with the above mentioned probe, radioactive rays within a living body can be detected but the radioactive ray generating part can not be observed.

Also, as shown in the publication of a Japanese utility model application publication No. 5168/1972, with a fiber scope provided with a radioactive ray detecting means, it is difficult to know the radioactive ray information while observing an observed part from an eyepiece part. That is to say, a radioactive ray information display means must be seen by separating an eye from the eyepiece part. Therefore, it is difficult to make the radioactive ray generating source and endoscope image correspond to each other. Particularly, it has been difficult to confirm the positions of a deep part cancer and lymphatic knot transfer.

In the observation with a fiber scope, as only the surface of a tissue can be observed, a cancer or the like in the deep part of the tissue can not be confirmed. It is difficult to make a radioactive ray generating source in the deep part of the tissue and its image correspond to each other.

OBJECT AND SUMMARY OF THE INVENTION

An object of the present invention is to provide a radioactive ray detecting endoscope whereby, for a radioactive ray generating source in the deep part of a tissue, the observed image and radioactive ray information can be simultaneously seen and it is easy to make the observed image and radioactive ray generating source correspond to each other.

Another object of the present invention is to provide a radioactive ray detecting endoscope whereby even the interior of a body cavity of a small diameter as a tubular cavity can be easily observed and can have radioactive rays detected.

A radioactive ray detecting endoscope of the present invention comprises an elongated insertable part, an ultrasonic imaging device provided in the tip part of the above mentioned insertable part and having a transmitting device transmitting ultrasonic waves toward an observed part and a receiving device receiving echoes from the observed part of the ultrasonic waves emitted from the above mentioned transmitting device and outputting a signal for forming an ultrasonic image. A radioactive ray detecting device is arrangeable in the tip part of the above mentioned insertable part and detects radioactive rays. Preferably, the observing direction of the above mentioned ultrasonic imaging device and the detecting direction of the above mentioned radioactive ray detecting device substantially coincide with each other. In this case, for example, the observing direction of the ultrasonic imaging device and the detecting direction of the radioactive ray detecting device will be on the side of the above mentioned insertable part.

The other features and advantages of the present invention will be apparent enough with the following explanation.

BRIEF DESCRIPTION OF THE DRAWINGS

FIG. 1 is an explanatory view showing the formation of an endoscope apparatus.

FIG. 2 is a sectioned view showing a tip part of an endoscope.

FIG. 7 is a perspective view showing the tip side of an endoscope.

FIG. 8 is an explanatory view showing a cross-section of the tip part of the endoscope.

FIG. 9 is an explanatory view showing a monitor picture image. FIG. 10 is an explanatory view showing a tip part of an endoscope. FIG. 11 is an explanatory view showing a monitor picture image. FIG. 12 is an explanatory view showing the formation of an endoscope apparatus. FIG. 13 is a plan view of a tip part of an endoscope. FIG. 15 is a sectioned view showing a tip part of an endoscope. FIG. 16 is a plan view of a solid state imaging device and radioactive ray detecting device. FIGS. 17 to 19 relate to the 11th embodiment of the present invention. FIG. 17 is an explanatory view showing the formation of an endoscope apparatus. FIG. 18 is a plan view of a tip part of an endoscope. FIG. 19 is a plan view of a tip part of an endoscope in a modification of the 11th embodiment.

FIGS. 20 to 22 relate to the 12th embodiment of the present invention. FIG. 20 is a sectioned view of an essential part of a tip part of an endoscope. FIGS. 21 and 22 are sectioned views of essential parts of a tip part of an endoscope in a modification of the 12th embodiment. FIG. 23 is a sectioned view of an essential part of a tip part of an endoscope. FIG. 24 is a sectioned view of an essential part of a tip part of an endoscope. FIG. 25 is a plan view of a tip part of an endoscope. FIG. 26 is a perspective view of a tip part of an endoscope. FIG. 27 to 29 relate to the 15th embodiment of the present invention. FIG. 27 is a sectioned view of an essential part of a tip part of an endoscope. FIG. 28 is a perspective view showing another example of a collimator. FIGS. 29(A) to (D) are explanatory views showing modifications of a collimator.

FIG. 32 is a sectioned view of an essential part of a tip part of an endoscope.

FIG. 33 is a sectioned view of an essential part of a tip part of an endoscope in a modification of the 18th embodiment.

FIGS. 34 to 41 relate to the 19th embodiment of the present invention.

FIG. 34 is an explanatory view showing the formation of an entire endoscope apparatus.

FIG. 35 is an explanatory view showing a monitor picture image.

FIG. 36 is a block diagram of a video signal processing circuit.

FIG. 37 is a block diagram showing the formation of a radioactive ray detecting means.

FIG. 38 is an explanatory view of a radioactive ray probe in which a radioactive ray detecting sensor part rotates.

FIG. 39 is an explanatory view of a monitor picture image displaying the radioactive ray measuring results obtained by rotating the radioactive ray detecting sensor part.

FIGS. 40(A) and (B) are sectioned views in the direction A-A' in FIG. 38 and are explanatory views of the fitting states of the radioactive ray detecting sensor.

FIG. 41 is an explanatory view of the formation of a radioactive ray detecting probe inserted through a sheath.

FIG. 42 is an explanatory view showing the formation of an entire endoscope apparatus.

FIG. 43 is an explanatory view showing a monitor picture image.

FIG. 45 is a block diagram for explaining a radioactive ray detecting endoscope apparatus with which a radioactive ray detector is systematized by a personal computer.

FIG. 46 is an explanatory view of a radioactive ray detecting apparatus whereby a laser cauterization can be made.

DETAILED DESCRIPTION OF PREFERRED EMBODIMENTS

Figure 1:
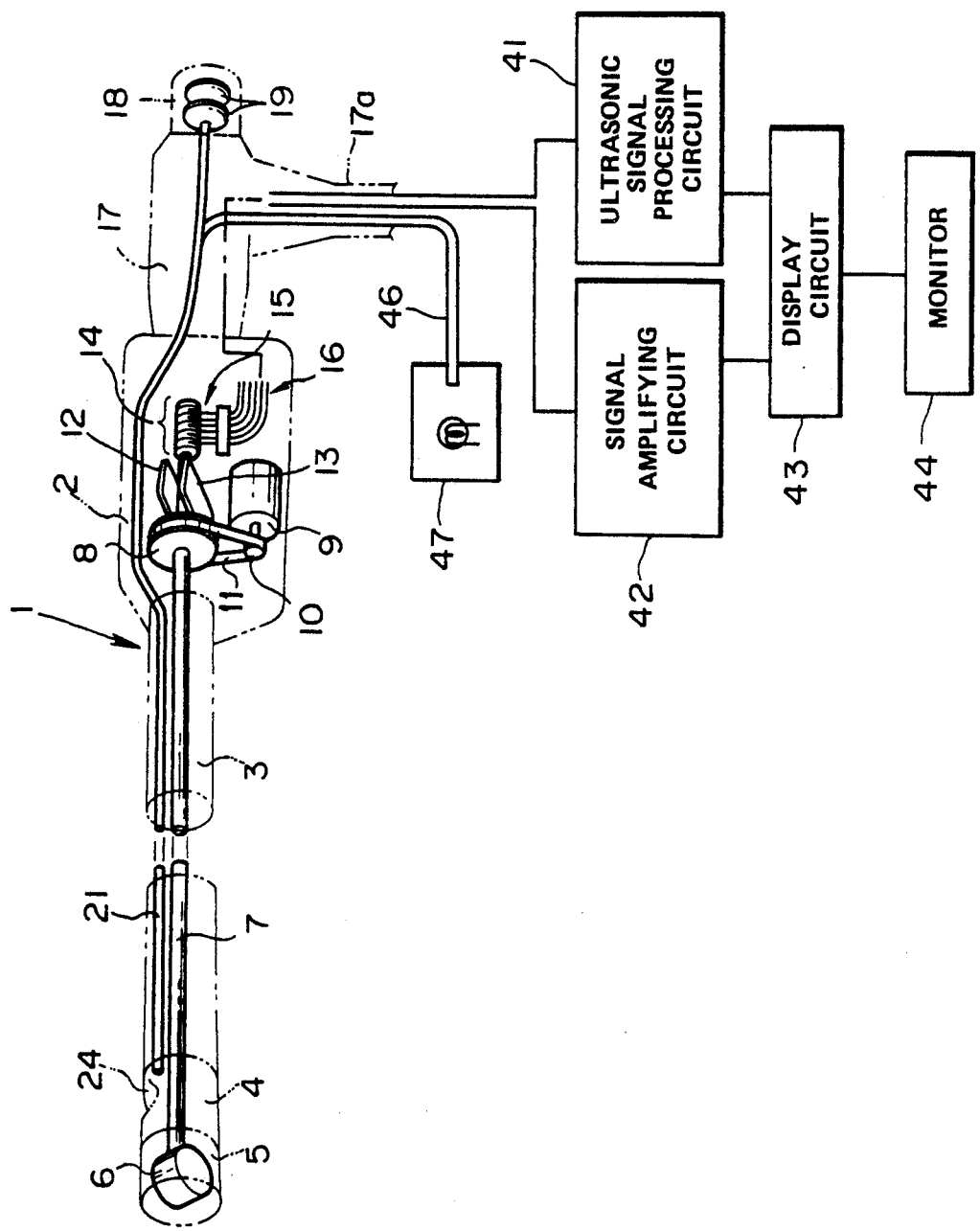
FIGS. 1 and 2 relate to the first embodiment of the present invention.
Figure 2:
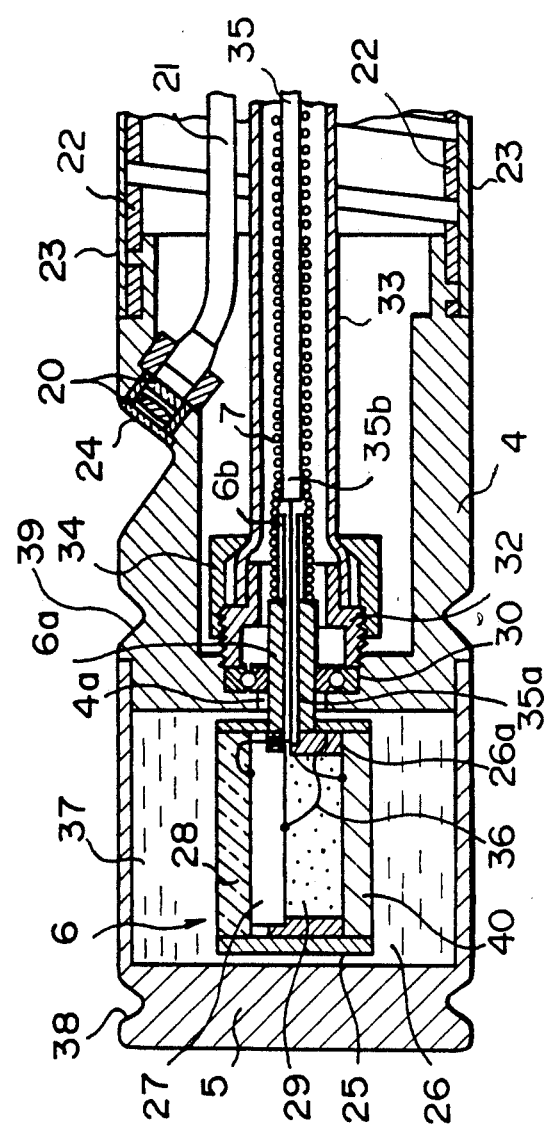

The first embodiment of the present invention is shown in FIGS. 1 and 2.

An ultrasonic endoscope 1 of this embodiment is formed mostly of a first operating part 2, a second operating part 17 and a body cavity insertable part consisting of a flexible tube part 3, tip forming part 4 and ultrasonic vibrator sheathing member 5 connected in the mentioned order on the tip side of the above mentioned first operating part 2. An ultrasonic vibrator part 6 is rotatably arranged within the above mentioned ultrasonic vibrator sheathing member 5 and is to be rotated and driven by a flexible shaft. As shown in FIG. 2, the above mentioned flexible shaft 7 is fixed at the tip to a handle part 6a of the vibrator part 6 extended out into the tip forming part 4, is inserted through the flexible tube part 3 and is then extended out at the rear end into the first operating part 2 and has a pulley 8 fixed at the rear end. A timing belt 11 is hung on this pulley 8 and an output pulley 10 fixed to the output shaft of a motor 9 which is a rotating driving source. An amplifying part 12 and pulser 13 are fixed to the above mentioned pulley 8. Further, a slip ring group 14 is fixed to the pulley 8. A brush group 15 is to contact this slip ring group 14. Lead wires 16 electrically connected to an ultrasonic observing apparatus (not illustrated) are connected to the above mentioned brush group 15.

The tip forming part 4 adjacent to the above mentioned ultrasonic vibrator sheathing member 5 is provided with an observing window and illuminating window. An objective lens 20 is provided inside the above mentioned observing window. The tip surface of an image guide 21 is arranged in the image forming position of this objective lens 20. In this embodiment, the visual field direction is set in the forward oblique view.

A light distributing lens not illustrated, is provided inside the above mentioned illuminating window. A light guide 46 is provided on the rear end side of this light distributing lens. The above mentioned image guide 21 and a light guide 46 are inserted through the flexible tube 3 and first operating part 2 and are then led into the second operating part 17. The image guide 21 is so arranged as to be opposed on the end surface to an eyepiece lens 19 within an eyepiece part 18 provided at the rear end of the second operating part 17. On the other hand, a light guide 46 is connected to a light source apparatus 47 through a universal cord 17a from the second operating part 7. In FIG. 1, an air feeding system and sucking system required for the function of the endoscope are omitted.

FIG. 2 is a magnified sectioned view showing the interiors of the above mentioned ultrasonic vibrator sheathing member 5 and tip forming part 4. The above mentioned sheathing member 5 is formed of a thick disc on the tip surface and of a cap-like short cylinder opened on the surface and has the ultrasonic vibrator part 6 rotably arranged within it. The tip forming part 4 tightly fitted at the tip to this sheathing member 5 is formed of a doughnut-like formed disc on the front end surface and is made integral with the above mentioned sheathing member 5 on the outer peripheral step part on the front end surface. A spiral tube 22 forming the flexible tube part 3 and a sheath 23 coating it are tightly fitted in the respective tip parts to the outer peripheral step part of the rear end part of this tip forming part 4. The above mentioned objective lens 20 is arranged through a cover glass 24 exposed outside in a part of the outer peripheral part of the above mentioned tip forming part 4. The above mentioned image guide 21 is opposed on the front end surface to this objective lens 20.

The ultrasonic vibrator part 6 arranged within the above mentioned sheathing member 5 is formed of an ultrasonic vibrator 27 fixed by a receiving member 26 within a vibrator fitting member 25 formed of a conductive material, an acoustic lens 28 arranged on a wave transmitting and receiving surface of this ultrasonic vibrator 27, a damping material 29 and a radioactive ray detecting device 40 bonded to the end surface on the side reverse to the ultrasonic vibrator 27 of this damping material 29. The above mentioned radioactive ray detecting device 40 is a semiconductor radioactive ray detecting device as, for example, of a PN junction type and is to output a current corresponding to the intensity of such radioactive rays as γ rays. The above mentioned vibrator fitting member 25 is formed of a short cylinder opened on the upper and lower surfaces and is so arranged that its axial direction may be at right angles with the axial direction of the insertable part. Therefore, the open end surfaces of the upper and lower surfaces of the vibrator fitting member 25 are opposed to the peripheral surface of the sheathing member 5. The above mentioned pipe-like handle part 6a is extended out sidewise in a part of the central part of the outer peripheral surface of this fitting member 25, forms a driving shaft rotating and scanning the ultrasonic vibrator 27 and is extended into the tip forming part 4 out of a central aperture 4a on the doughnut-like front end surface of the tip forming part 4.

Within the above mentioned thus formed vibrator fitting member 25, in a position from outside in the middle, the ultrasonic vibrator 27 is horizontally fixed by the receiving member 26 with its wave transmitting and receiving surface directed toward the upper opened end surface and the acoustic lens 28 which is also a coordinating layer is fixed on this wave transmitting and receiving surface. On the side reverse to the wave transmitting and receiving surface, the receiving member 26 is filled with the damping material 29. The handle part 6a extended out into the tip forming part 4 is rotatably borne by a bearing member 30 such as a bearing fixed to the tip forming part 4. A flexible shaft 7 formed by winding a conductive resilient wire like a closely wound coil is tightly fitted and fixed at the tip to a fine diameter part 6b formed by a step on the outer peripheral surface in the rear end part of this handle part 6a. This flexible shaft 7 may be formed as doubly wound. Also, within the tip forming part 4, a fixing member 32 for integrally fitting the above mentioned bearing member 30 to the tip forming part 4 is screwed into the tip forming part 4. A guide tube 33 coating the above mentioned flexible shaft 7 is fitted to this fixing member 32 as fastened with nut 34.

A conductive wire 35 is inserted through the above mentioned flexible shaft to transmit a transmitting driving pulse signal to the above mentioned ultrasonic vibrator 27, to transmit a receiving signal of the ultrasonic vibrator 27 to the outside amplifier and to transmit a signal from the radioactive ray detecting device 40 to the outside. This conductive wire 35 is formed of a wire coated with an insulative coating 35b. An insulatively coated lead wire 35a inserted through its center part passes as a signal transmitting line through the above mentioned pipe-like handle part 6a and is connected to a signal line terminal of the ultrasonic vibrator 27 within the vibrator fitting member 25. The ground line terminal of the ultrasonic vibrator 27 is connected to the above mentioned vibrator fitting member 25 through the aperture 26a of the receiving member 26 by the conductive wire 36. This conductive wire 35 and the flexible shaft 7 to which the conductive wire 36 of the ground line is electrically connected through the conductive handle part 6a form a conventional coaxial cable and are connected respectively to the amplifying part 12 and pulser 13.

The lead wire 16 connected to the above mentioned amplifying part 12 and pulser 13 through the pulley 8, slip ring group 14 and brush group 15 is inserted through the universal cord 17a and is connected to an ultrasonic signal processing circuit 41 within the ultrasonic observing apparatus.

The conductive wire connected to the above mentioned radioactive ray detecting device 40 is inserted through the universal cord 17a and is connected to a signal amplifying circuit 42.

The output signals of the above mentioned ultrasonic signal processing circuit 41 and signal amplifying circuit 42 will be input into a display circuit 43 and the output signal of this display circuit 43 will be input into a monitor 44 and an ultrasonic image and such radioactive ray information as the intensity of the radioactive rays will be displayed in this monitor 44.

The interior of the above mentioned ultrasonic vibrator sheathing member 5 is filled with an ultrasonic wave transmitting medium 37 consisting of an ultrasonic wave transmitting liquid and further the guide tube 33 is also filled with this transmitting medium 3 through the aperture 4a and bearing member 30 to reduce the friction between the flexible shaft 7 and guide tube 33. V-grooves 38 and 39 are made respectively on the outer peripheral surface of the thick tip part of the above mentioned sheathing member 5 and the outer peripheral surface from the front part of the tip forming part 4 and are parts to be fitted and fixed with a balloon to acoustically closely contact the body cavity wall and ultrasonic wave transmitting part with each other so that no air space may be formed. In the drawing, an air feeding hole and air feeding path for inflating the balloon are omitted.

The operation of the thus formed ultrasonic endoscope 1 in this embodiment shall be explained in the following.

When inspecting a cancer or the like by using the ultrasonic endoscope 1 of this embodiment, at a predetermined time before the inspection, a cancer resistor marked with a radio-isotope or a deoxyglucose likely to concentrate on a cancer is injected into the body by venous injection or the like. Such a reagent will concentrate on the cancer and radioactive rays, for example, rays will be emitted from the cancer.

Before the insertable part of the ultrasonic endoscope 1 is inserted into the body cavity, a well known pipe-like balloon (not illustrated) will be fitted to the tip part by being fixed at both ends to the above mentioned V-grooves 38 and 39. Then, the above mentioned insertable part will be inserted into the body cavity. The illuminating light emitted from the light source apparatus 47 will be radiated to an object through the light guide 46. The object image by this illuminating light will be observed by the observing optical system comprising the objective lens 20, image guide 21 and eyepiece lens 19.

The ultrasonic endoscope 1 of this embodiment is of a radial mechanical scanning system mechanically rotating the ultrasonic vibrator 27. A transmitting pulse will be delivered to the above mentioned ultrasonic vibrator 27 from the ultrasonic wave observing apparatus, the ultrasonic vibrator 27 will be driven by this transmitting pulse and an ultrasonic pulse will be emitted toward a living body. This ultrasonic pulse will be reflected in the boundary of tissues within the living body, will return as an echo to the ultrasonic vibrator 27 and will be converted to an electric signal. This electric signal will be processed in the ultrasonic signal processing circuit 41 within the above mentioned ultrasonic wave observing apparatus. The signal from this ultrasonic signal processing circuit 41 will be input into the monitor 44 through the display circuit 43 and an ultrasonic image, that is, a sectioned image of the tissue will be displayed in the monitor 44.

Also, in this embodiment, radioactive rays can be detected by the radioactive ray detecting device 40. An ultrasonic image and radioactive ray information such as the intensity of radioactive rays will be displayed in the above mentioned monitor 44. In such a case, by rotating the ultrasonic vibrator 27 and radioactive ray detecting device 40, the radioactive rays on the entire periphery may be detected simultaneously with the observation of the ultrasonic image. By stopping in a predetermined position the ultrasonic vibrator 27 and radioactive ray detecting device 40, radioactive rays in a part in a specific direction may be detected.

By providing a radioactive ray attenuating member on one surface of the radioactive ray detecting device 40, radioactive rays only in the direction identical with or reverse to the ultrasonic wave observing direction can be detected.

In case the radioactive ray detecting device 40 is sensitive to not only radioactive rays but also light, when the radioactive rays are being detected with the above mentioned radioactive ray detecting device 40, it will be desirable to keep the illuminating light reduced or extinguished.

Thus, according to this embodiment, with the ultrasonic endoscope 1, an ultrasonic image of the deep part of the tissue in the observed part can be obtained and the radioactive rays from this observed part can be detected. Therefore, by observing the ultrasonic image and detecting the radioactive rays of the same part, the presence or absence of a cancer or lymphatic knot transfer in the deep part of a tissue and the position including the position in the depth direction can be easily confirmed and the ultrasonic image can be observed. Thereby, the operating method and curing method can be easily and positively determined.

The optical observation, ultrasonic observation and radioactive ray detection in the same part are possible and the optical image or ultrasonic image and the radioactive ray generating source can be easily made to correspond to each other.

As the radioactive ray detecting device 40 is integrally provided on the back surface of the ultrasonic vibrator 27, the actually fitting space may be smaller than in the case that they are separately arranged, it is not necessary to enlarge the outside diameter and length of the tip part and the burden on the patient can be reduced.

As the ultrasonic image is output as an electric signal, the image of the observed position can be displayed in such a display means as the monitor 44, the image of the observed part and radioactive ray information can be simultaneously seen and the image of the observed part and the radioactive ray generating source can be easily made to correspond to each other.

The means of observing the optical image may be a solid state imaging device provided in the image forming position of the objective lens 20 instead of the image guide 21.

Figure 3:
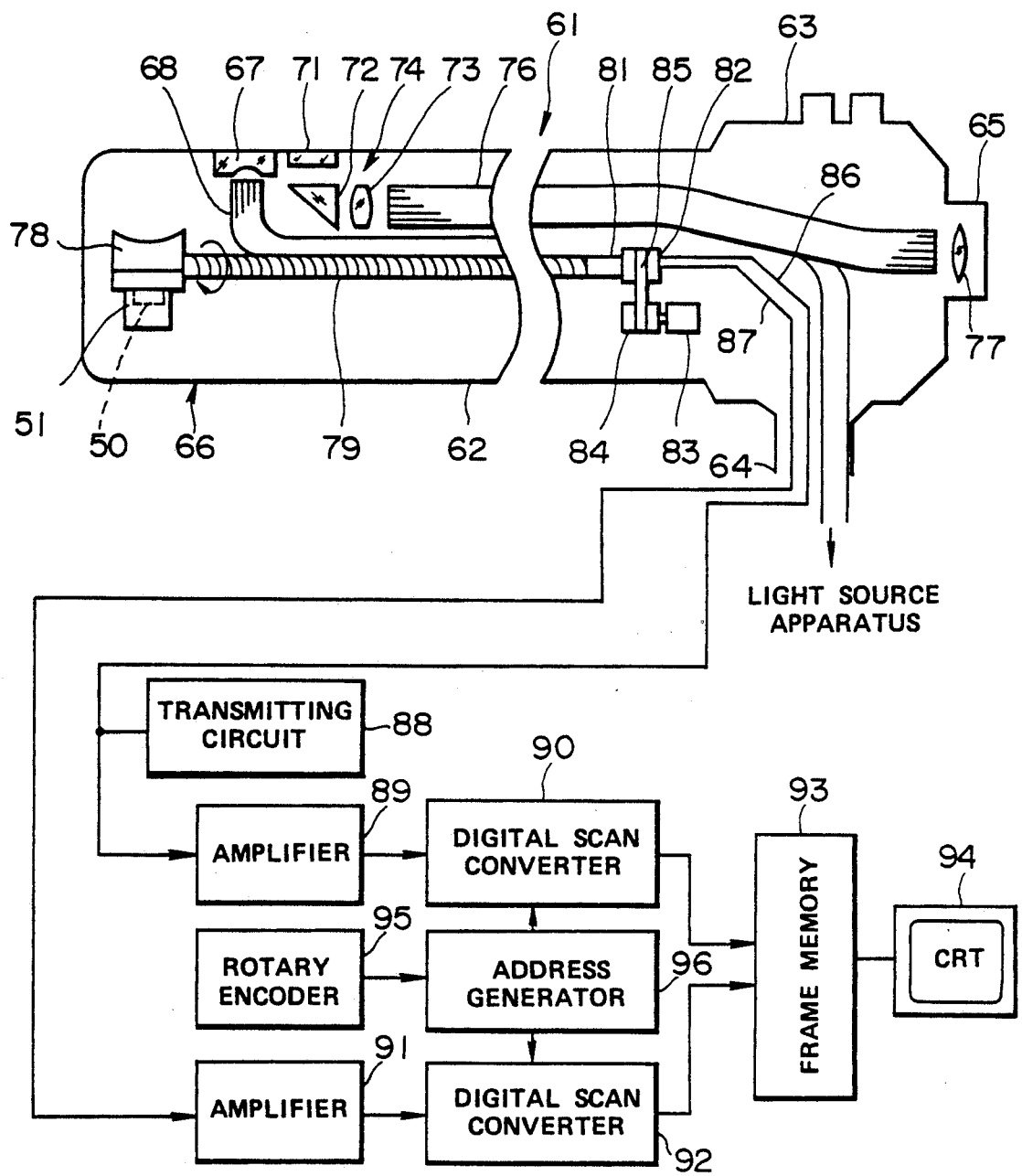
FIG. 3 is an explanatory view showing an endoscope apparatus of the second embodiment of the present invention.

The second embodiment of the present invention is shown in FIG. 3.

This embodiment is an example of a side view type ultrasonic endoscope.

As shown in FIG. 3, an ultrasonic endoscope 61 of this embodiment is provided with an elongated, for example, flexible insertable part 62 and a thick operating part 63 connected to this insertable part at the rear end a flexible universal cord 64 is extended sidewise from the above mentioned operating part 63 which is provided at the rear end with an eyepiece part 65.

The tip part 66 of the above mentioned insertable part 62 is provided on one side with an illuminating window and observing window in the mentioned order from the tip side. A light distributing lens 67 is fitted to the above mentioned illuminating window. A light guide 68 is provided on the rear end side of this light distributing lens 67, is inserted through the insertable part 62, operating part 63 and universal cord 64 and is connected to a light source apparatus (not illustrated).

A cover glass 71 is fitted to the above mentioned observing window. An objective optical system 74 having a reflecting prism 72 and lens 73 is arranged inside this cover glass 71. An image guide 76 consisting of a fiber bundle is arranged on the tip surface in the image forming position of this objective optical system 74, is inserted through the insertable part 62 and operating part 63, is extended to the eyepiece part 65 and is opposed on the rear end surface to an eyepiece lens 77 provided within the eyepiece part 65 so that an object image formed by the objective optical system 74 and transmitted by the image guide 76 may be observed from the above mentioned eyepiece part 65.

An ultrasonic vibrator (probe) 78 and a radioactive ray detecting device (for example, of cadmium telluride) 50 provided within a collimator 51 as jointed with each other on the back surfaces to be integral are arranged on the tip side of the above mentioned tip part 66. The above mentioned collimator 51 is a member having at least one aperture in the radioactive ray detecting direction and made of a radioactive ray attenuating material which is material weakening the intensity of radioactive rays for example, lead, tungsten, stainless steel, lead glass (made by mixing lead at a high rate into a plastic or epoxy resin) concrete, steel (the older, the better) or mercury. The above mentioned ultrasonic vibrator 78 and radioactive ray detecting device 50 are respectively arranged toward the side of the tip part 66 and are rotatable with the axis parallel with the lengthwise direction of the insertable part 62 as a center. A flexible shaft 79 inserted rotatably through the insertable part 62 is connected at the tip to these ultrasonic vibrator 78 and radioactive ray detecting device 50 and at the rear end with a driving shaft 81 fitted, for example, with a pulley 82. A motor 83 is provided within the above mentioned operating part 63 or an auxiliary operating part provided on the tip side of this operating part 63. A pulley 84 is fitted to the driving shaft of this motor 83. Both pulleys 82 and 84 are connected through a belt 85. Therefore, when the above mentioned motor 83 is rotated, the ultrasonic vibrator 78 and radioactive ray detecting device 50 will be rotated through the flexible shaft 79.

A signal line 86 connected to the above mentioned ultrasonic vibrator 78 is passed through the above mentioned flexible shaft 79, is inserted through the universal cord 64 and is connected to an ultrasonic wave observing apparatus (not illustrated). On the other hand, a signal line 87 connected to the above mentioned radioactive ray detecting device 50 is passed through the above mentioned flexible shaft 79, is inserted through the universal cord 64 and is connected to a radioactive ray measuring apparatus.

In the illustrated ultrasonic observing apparatus and radioactive ray measuring apparatus, an amplifier 89 connected with the signal line 86 through a transmitting circuit 88 is connected on the output side to a digital scan converter 90, on the other hand, an amplifier 91 connected with the signal line 87 is connected on the output side to a digital scan converter 92 and both digital scan converters 90 and 92 are connected on the output sides to a CRT monitor 94 through a frame memory 93 and are connected with a rotary converter 95 through an address generator 96. The signals of the ultrasonic vibrator 78 and radioactive ray detecting device 50 will be made ultrasonic B mode image data on the digital scan converters 90 and 92 from the coordinate signal of a rotary encoder 95 and data displaying the radioactive ray source by a character and the signals of these two digital scan converters 90 and 92 will be synthesized by the frame memory 93 and will be displayed in the CRT monitor 94.

The ultrasonic endoscope 61 of this embodiment is of a radial mechanical scanning system mechanically rotating the ultrasonic vibrator 78. A transmitting pulse will be delivered to the above mentioned ultrasonic vibrator 78 from the ultrasonic observing apparatus, the ultrasonic vibrator will be driven by this transmitting pulse and an ultrasonic pulse will be emitted toward a living body, will be reflected by the boundary of tissues within the living body, will be returned as an echo to the ultrasonic vibrator and will be converted to an electric signal. This electric signal will be processed by the above mentioned ultrasonic wave observing apparatus. The signal from this ultrasonic wave observing apparatus will be input into the monitor 94 in which an ultrasonic image will be displayed.

In this embodiment, radioactive rays can be detected by the radioactive ray detecting device 50. In this case, the ultrasonic vibrator 78 and radioactive ray detecting device 50 may be rotated so as to detect the radioactive rays on the entire periphery simultaneously with the observation of the ultrasonic image and the ultrasonic vibrator 78 and radioactive ray detecting device 50 may be stopped in a predetermined position to detect radioactive rays in a part in a specific direction.

In this embodiment, in an endoscope of a side view type in both optical observing direction and ultrasonic observing direction, the radioactive ray detecting direction by the radioactive ray detecting device 50 is also set sidewise and radioactive rays can be easily detected even in a body cavity of a small diameter as a tubular body cavity.

The other operations and effects are the same as in the first embodiment.

Figure 4:
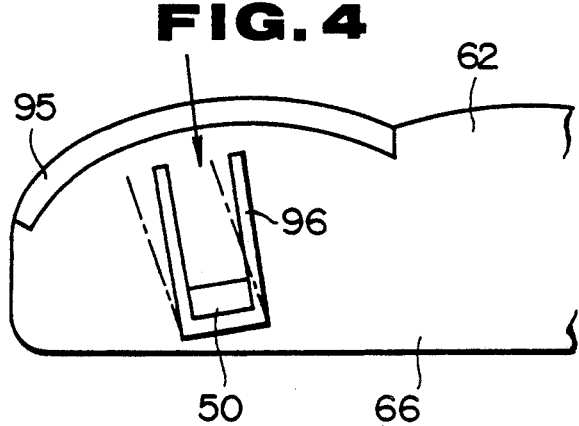
FIG. 4 is an explanatory view showing a tip part of an endoscope in the third embodiment of the present invention.

The third embodiment of the present invention is shown in FIG. 4.

In this embodiment, a convex type vibrator 95 transmitting radioactive rays is arranged on the side of the tip part 66 of an insertable part 62 and a radioactive ray detecting device 50 containing a collimator 96 is provided in the inner direction of this vibrator 95. The convex type is to move an ultrasonic beam in a sector and is one of electronic sector scannings. The detecting device 50 may be rotatable.

Figure 5:
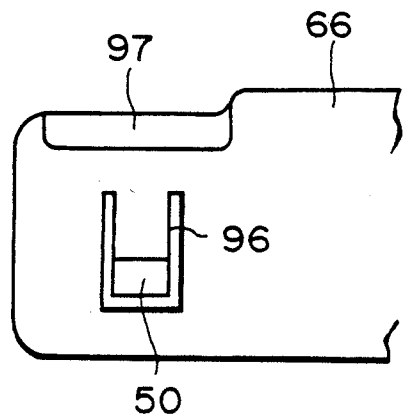
FIG. 5 is an explanatory view showing a tip part of an endoscope in the fourth embodiment of the present invention.

The fourth embodiment of the present invention is shown in FIG. 5.

In this embodiment, a vibrator 97 of an electronic sector scanning system, for example, of a phase controlling type is provided on the side of the tip part 66 and the radioactive ray detecting device 50 containing the collimator 96 is provided inside this vibrator 97. The above mentioned vibrator 97 may be of an electronic linear scanning system.

Figure 6:
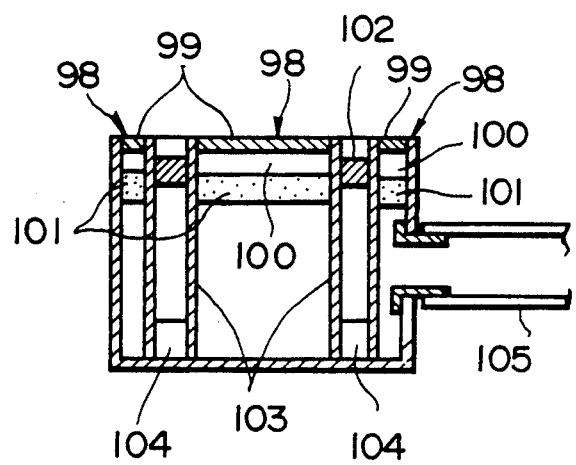
FIG. 6 is a sectioned view showing a rotating part within a tip part of an insertable part of an endoscope in the fifth embodiment of the present invention.

The fifth embodiment of the present invention is shown in FIG. 6.

In this embodiment, the central part and ring-like outer layer part are made an ultrasonic wave receiving part 98 and the ring-like (concentric circular) intermediate layer part is made a radioactive ray detecting part. The reference numeral 99 represents an ultrasonic lens, 100 represents a vibrator, 101 represents a damper, 102 represents lead, 103 represents a collimator, 104 represents a detecting device made of cadmium telluride and 105 represents a flexible shaft.

Figure 7:
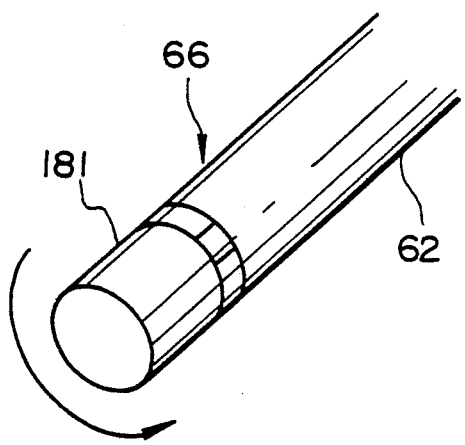
FIGS. 7 to 9 relate to the sixth embodiment of the present invention.
Figure 8:
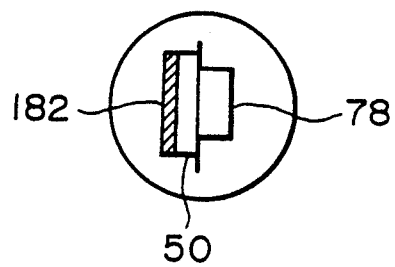
Figure 9:
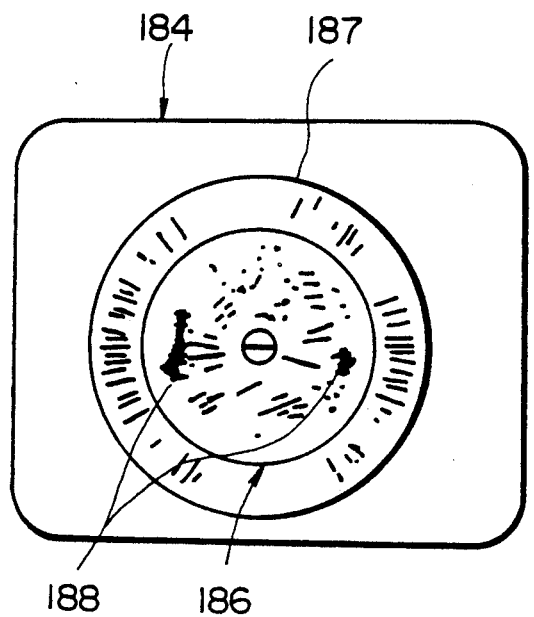

The sixth embodiment of the present invention is shown in FIGS. 7 to 9.

In this embodiment, as shown in FIG. 7, a rotating part 181 rotatable with the axis of the insertable part 62 as a center is provided on the tip side of the tip part 66. As shown in FIG. 8, an ultrasonic vibrator 78 is provided within the above mentioned rotating part 181. A radioactive ray detecting device 50 is jointed to this ultrasonic vibrator 78 on the back surface. Such radioactive ray shield 182 as lead is joined to this radioactive ray detecting device 50 on the surface on the side reverse to the ultrasonic vibrator 78. Therefore, in this embodiment, the ultrasonic wave observing direction by the ultrasonic vibrator 78 and the radioactive ray detecting direction by the radioactive ray detecting device 50 will coincide with each other. These ultrasonic vibrator 78, radioactive ray detecting device 50 and radioactive ray shield 182 are rotatable integrally with the above mentioned rotating part 181.

The above mentioned rotating part 181 will be rotated as connected to such flexible shaft 79 as is shown, for example, in FIG. 3. When the above mentioned rotating part 181 is rotated, the ultrasonic vibrator 78 and radioactive ray detecting device 50 will be integrally rotated, an ultrasonic image by the radial mechanical scanning system will be obtained and, at the same, radioactive rays will be detected.

The ultrasonic image by the above mentioned ultrasonic vibrator 78 and the radioactive ray information by the radioactive ray detecting device 50 will be simultaneously displayed in the same monitor as shown in FIG. 9. That is to say, for example, a circular ultrasonic image 186 will be displayed in the central part of the picture surface of a monitor 184 and a radioactive ray information 187 will be displayed around this ultrasonic image 186. The above mentioned radioactive ray information 187 will be displayed, for example, by radial lines. The position of the radioactive ray generating source will be shown by the position of these lines and the radioactive ray intensity will be shown by the density of the lines. In FIG. 9, the reference numeral 188 represents a tumor. In the radioactive ray information 187, the density of the lines in the position corresponding to the above mentioned tumor 188 will be high and the tumor will be thereby identified.

With a conventional radioactive ray detector, though the position of such a tumor as cancer can be detected, the size and structure of the tumor have not been able to be known. On the contrary, with an ultrasonic endoscope, though the structure within a tissue can be known, whether it is of a tumor or not has been difficult to judge.

On the other hand, according to this embodiment, as the ultrasonic wave observation and radioactive ray detection of the same part can be simultaneously made and the ultrasonic image and radioactive ray information, that is, tumor position information can be displayed simultaneously on the monitor 184, the structure of the tumor can be analyzed simultaneously with the discovery of the tumor.

The other formations, operations and effects are the same as in the second embodiment.

Figure 10:
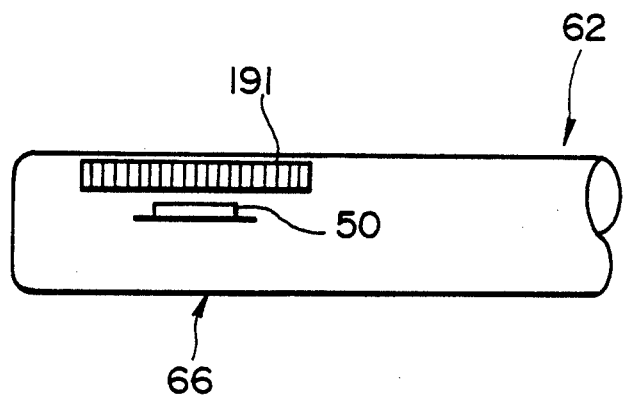
FIGS. 10 and 11 relate to the seventh embodiment of the present invention.
Figure 11:
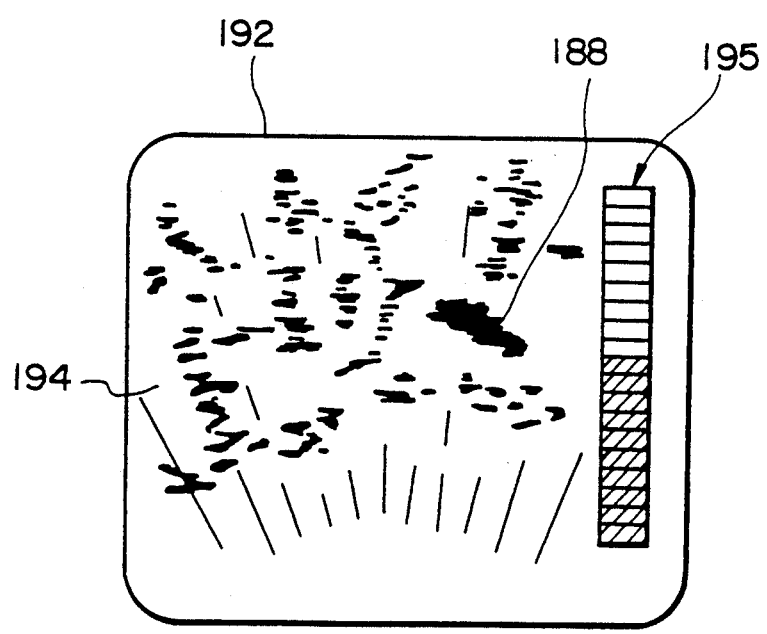

The seventh embodiment of the present invention is shown in FIGS. 10 and 11.

This embodiment is an example of an ultrasonic endoscope of a linear electronic scanning system.

As shown in FIG. 10, an ultrasonic probe 191 made by arranging many vibrating devices is provided on one side of the tip part 66 of the insertable part 62. A radioactive ray detecting device 50 is provided on the back surface of this ultrasonic probe 191.

The ultrasonic image by the above mentioned ultrasonic probe 191 and the radioactive ray information by the radioactive ray detecting device 50 will be simultaneously displayed on the same monitor 192 as shown in FIG. 11. That is to say, on the monitor 192, a radioactive ray information 195 will be displayed on the side of an ultrasonic image 194 and will show the radioactive ray intensity by the height of the bar graph.

The other formations, operations and effects are the same as in the sixth embodiment.

Figure 12:
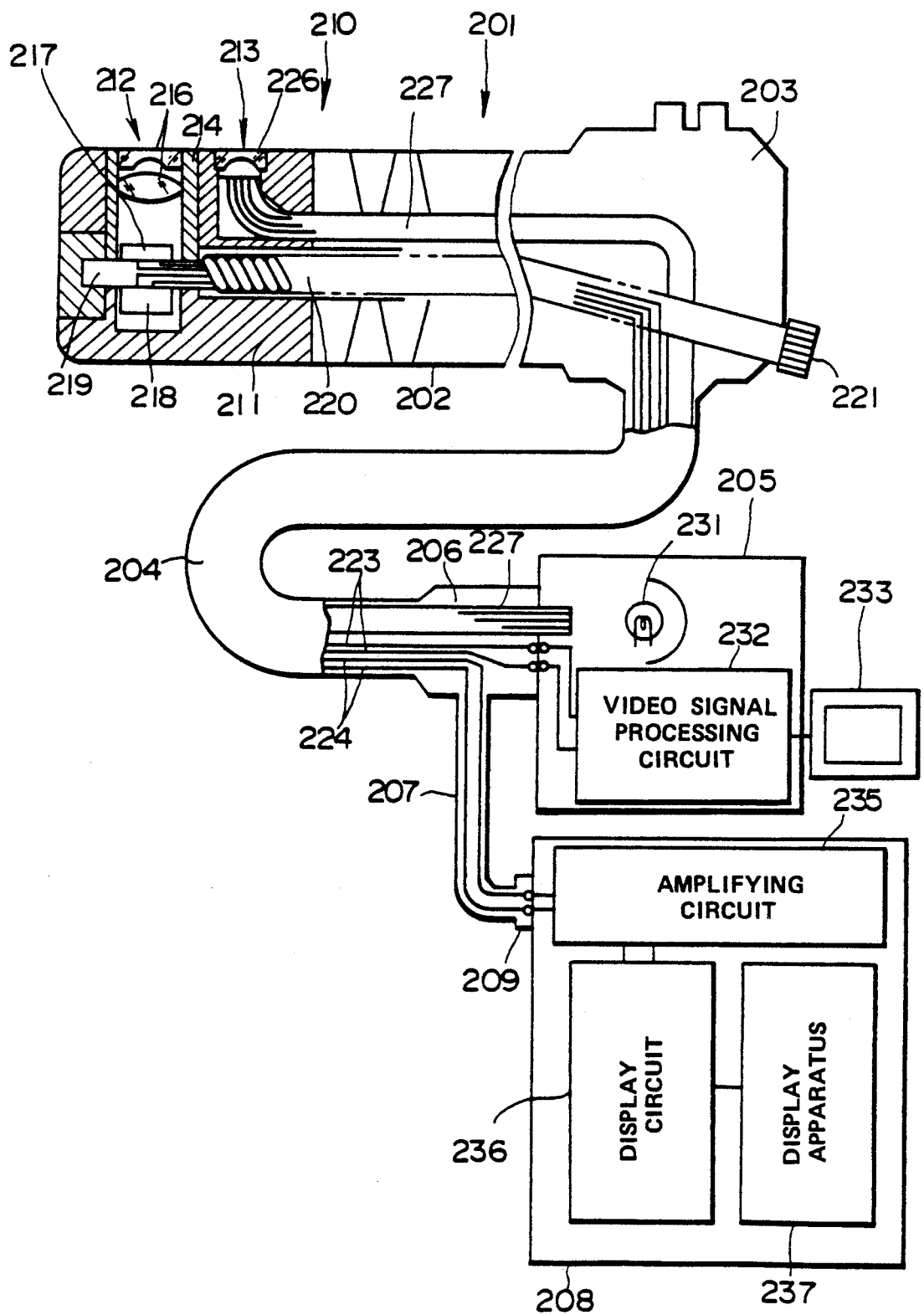
FIGS. 12 and 13 relate to the eighth embodiment of the present invention.
Figure 13:
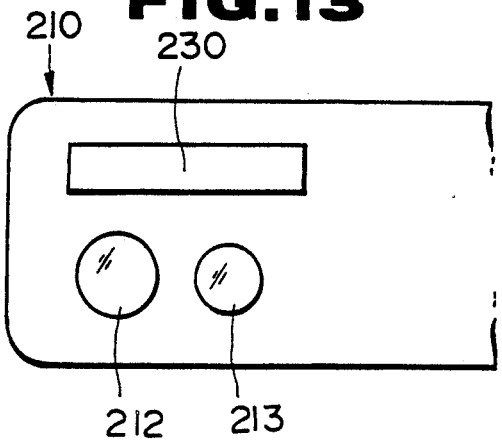

The eighth embodiment of the present invention is shown in FIGS. 12 and 13.

This embodiment is an example of a side view type endoscope.

An endoscope 201 is provided with an elongated, for example, flexible insertable part 202 and a thick operating part 203 connected to this insertable part 202 at the rear end. A flexible universal cord 204 is extended sidewise from the above mentioned operating part 203 and is provided at the end with a connector 206 removably connected to a video processor 205. A signal cable 207 is extended from the above mentioned connector 206 and is provided at the end with a connector 209 removably connected to a radioactive ray measuring apparatus 208.

The tip part 210 of the above mentioned insertable part 202 is provided with a rigid tip body 211 provided on one side with an observing window 212 and illuminating window 213 in the mentioned order from the tip side as shown in FIG. 13. An ultrasonic probe 230, for example, of an electronic sector scanning system or electronic linear scanning system is arranged on the side of the observing window 212 and illuminating window 213. A cylindrical collimator 214 made of such radioactive ray attenuating material as lead is fitted inside the above mentioned observing window 212. An objective lens system 216 is fitted on the observing window 212 side within this collimator 214. A solid state imaging device 217 as a CCD and radioactive ray detecting device 218 made integral as jointed to each other on the back surfaces are arranged on the inner side of the above mentioned collimator 214 and are rotatably fitted to the tip body 211 through a switching shaft 219. By rotating the above mentioned switching shaft 219, one of the solid state imaging device 217 and radioactive ray detecting device 218 can be selectively opposed to the objective lens system 216. A flexible shaft 220 is connected to the above mentioned switching shaft 219, is inserted through the insertable part 202 and operating part 203, is led out of the operating part 203 at the rear end and is fitted at the end with a rotating grip 221. By rotating this rotating grip 221, one of the above mentioned solid state imaging device 217 and radioactive ray detecting device 218 can be opposed to the objective lens system 216 and can be fixed in the position opposed to the objective lens system 216 by a clicking mechanism or the like (not illustrated).

In case the above mentioned solid state imaging device 217 is opposed to the objective lens system 216, it will be arranged in the image forming position of this objective lens system 216. The above mentioned radioactive ray detecting device 218 is a semiconductor radioactive ray detecting device as, for example, of a PN junction type and will output a current corresponding to the intensity of such radioactive rays as γ rays.

Signal lines 223 connected to the above mentioned solid state imaging device 217 are passed through the above 217 are passed through the above mentioned flexible shaft 220, are inserted through the universal cord 204 and are connected to a connector 206. Signal lines (not illustrated) connected to the above mentioned ultrasonic probe 230 are inserted through the insertable part 202, operating part 203 and universal cord 204 and are connected to the above mentioned connector 206. On the other hand, signal lines 224 connected to the above mentioned radioactive ray detecting device 218 are passed through the above mentioned flexible shaft 220, are inserted through the universal cord 204 and signal cord 207 and are connected to a connector 209.

A light distributing lens 226 is fitted to the above mentioned illuminating window 213 and is connected at the rear end with a light guide 227 consisting of a fiber bundle, inserted through the insertable part 202, operating part 203 and universal cord 204 and connected at the entrance end to the connector 206.

A lamp 231 is provided within the above mentioned video processor 205 so that the light emitted from this lamp 231 may enter the above mentioned light guide 227 at the entrance end. A video signal processing circuit 232 connected to the solid state imaging device 217 and ultrasonic probe 230 through the signal lines and connector 206 is provided within the above mentioned video processor 205. This video signal processing circuit 232 will drive the above mentioned solid state imaging device 217, will process the output signal of this solid state imaging device so as to be a video signal, will transmit a transmitting pulse to the ultrasonic probe 230 and will process the output signal of this ultrasonic probe 217. The video signal output from this video signal processing circuit 232 will be input into a monitor 233 in which the optical image and ultrasonic image of the observed part will be displayed. In the monitor 233, the optical image and ultrasonic image may be displayed as switched to each other or may be displayed on the same picture surface. The optical image and ultrasonic image may be displayed respectively on separate monitors.

An amplifying circuit 235 connected to the radioactive ray detecting device 218 through the signal lines 224 and connector 209 is provided within the above mentioned radioactive ray measuring apparatus 208. The output signal of the above mentioned radioactive ray detecting device 218 will be amplified by the above mentioned amplifying circuit 235, then will be input into a display circuit 236 and will be processed in this display circuit 236 so as to be able to display such radioactive ray information as the intensity of radioactive rays. The output signal of this display circuit 236 will be input into a display apparatus 237 in which such radioactive ray information as the intensity of radioactive rays will be displayed.

The operation of this embodiment shall be explained in the following.

In the case of inspecting a cancer or the like by using the endoscope 201 of this embodiment, at a predetermined time before the inspection, a cancer resistor marked with a radioisotope or a deoxyglucose or the like likely to concentrate on a cancer will be injected into the body by venous injection or the like. Such reagent will concentrate on a cancer and radioactive rays, for example, γ rays will be emitted from the cancer.

When the insertable part 202 of the above mentioned endoscope 201 is inserted into the body cavity and the lamp 231 within the video processor 205 is lighted, the illuminating light emitted from this lamp 231 will enter the light guide 227 of the endoscope 201 at the entrance end, will be led to the tip part 210 by the light guide 227, will pass through the light distributing lens and will be radiated to an object.

In the case of observing the optical image of this object, the rotating grip 221 will be operated to oppose the solid state imaging device 217 to the objective lens system 216. The light returning from the object by the above mentioned illuminating light will be made to form an image on the solid state imaging device 217 by the objective lens system 216. The object image imaged by this solid state imaging device 217 will be displayed on the monitor 233.

By using the ultrasonic probe 230 simultaneously with the observation of the optical image, the ultrasonic image, that is, the sectioned image of the tissue can be displayed and observed on the monitor 233.

Thus, when, for example, a part likely to be an affected part is discovered while the optical image and ultrasonic image of the observed part are being observed on the monitor 233, the above mentioned rotating grip 221 will be rotated to rotate the switching shaft 219 to oppose the radioactive ray detecting device 218 to the objective lens system 216. When the observing window 212 is opposed to a cancer, such radioactive rays as γ rays emitted from this cancer will enter through the above mentioned observing window, will reach the above mentioned radioactive ray detecting device 218 and will be detected by this radioactive ray detecting device 218. The intensity or the like of the radioactive rays detected by this radioactive ray detecting device 218 will be displayed in the displaying apparatus 237.

By using the ultrasonic probe 230 simultaneously with the detection of radioactive rays, the ultrasonic image, that is, the sectioned image of the tissue can be displayed and observed on the monitor 233.

In case the above mentioned radioactive ray detecting device 218 is sensitive not only to radioactive rays but also to light, it will be desirable to keep the lamp 231 dimmed or extinguished.

Thus, according to this embodiment, with the endoscope 201, the optical image of the observe part can be observed and the radioactive rays from this observed part can be detected. The ultrasonic image can be observed simultaneously with the radioactive ray detection. Therefore, the presence or absence and position of a deep part cancer or lymphatic knot transfer can be easily confirmed and the operating method and curing method can be easily and positively determined.

As the radioactive ray detecting device 218 is integrally provided on the back surface of the solid state imaging device 217, as compared with the case that they are provided as arranged separately, the actual fitting space may be smaller, the outside diameter and length of the rigid tip part 210 need not be made larger and the burden on the patient can be reduced.

The observation and radioactive ray detection of the same part are possible. The endoscope image and the radioactive ray generating source can be easily made to correspond to each other.

Figure 14:
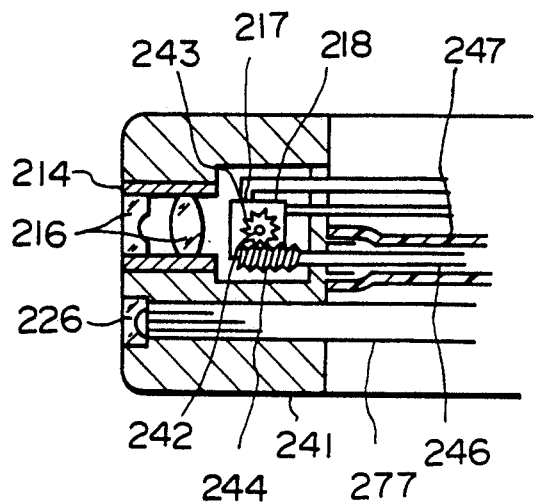
FIG. 14 is a sectioned view showing a tip part of an endoscope in the ninth embodiment of the present invention.

The ninth embodiment of the present invention is shown in FIG. 14.

This embodiment is an example of a straight view type endoscope

As shown in FIG. 14, in a tip body 241, an observing through hole and illuminating through hole are formed parallelly in the lengthwise direction of an insertable part 202. An objective lens system 216 held by a cylindrical collimator 214 is fitted to the above mentioned observing through hole. A solid state imaging device 217 and radioactive ray detecting device 218 integrally jointed with each detecting device 218 integrally jointed with each other on the back surfaces are arranged in the rear of this objective lens system 216, are rotatable with the axis 242 intersecting at right angles with the lengthwise direction of the insertable part 202 as a center and are fitted with a worm wheel 243 having the above mentioned axis 242 as a rotation center and meshed with a worm 244. A flexible shaft 246 is connected to this worm 244, is inserted through the insertable part 202 and operating part 203 the same as in the ninth embodiment and is connected to a rotating grip 221. The above mentioned flexible shaft 246 is coated with a tube 247 connected to the above mentioned tip body 241 at the rear end.

A light distributing lens 226 is fitted on the tip side of the above mentioned illuminating through hole and is connected with a light guide 227 on the rear end side.

In this embodiment, when the rotating grip 221 is operated to rotate the worm 244, one of the solid state imaging device 217 and radioactive ray detecting device 218 will be opposed to the objective lens system 216.

The ultrasonic probe 230 may be provided o the side of the tip body 241 the same as in the eighth embodiment or such small probe as of a sector mechanical scanning system may be provided at the front end of the tip body 241.

The other formations, operations and effects are the same as in the eighth embodiment.

Figure 15:
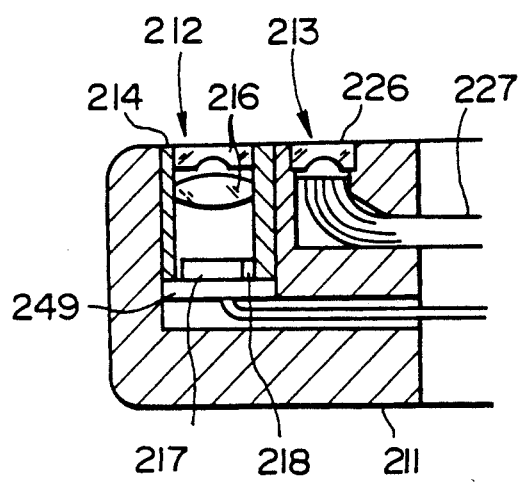
FIGS. 15 and 16 relate to the tenth embodiment of the present invention.
Figure 16:

The tenth embodiment of the present invention is shown in FIGS. 15 and 16.

This embodiment is an example of a side view type endoscope the same as in the eighth embodiment.

In this embodiment, a solid state imaging device 217 and radioactive ray detecting device 218 formed integrally on the same plane of a base 249 are arranged on the inner side of a collimator 214 so that an optical image formed by an objective lens system 216 may be imaged by the solid state imaging device 217 and radioactive rays entering through an observing window 212 may be detected by the radioactive ray detecting device 218.

According to this embodiment, such means of switching the solid state imaging device 217 and radioactive ray detecting device 218 to each other as in the eighth and ninth embodiments is not required and the formation is simple.

The radioactive rays in the part being observed can be detected substantially without any time difference.

The other formations, operations and effects are the same as in the eighth embodiment.

Figure 17:
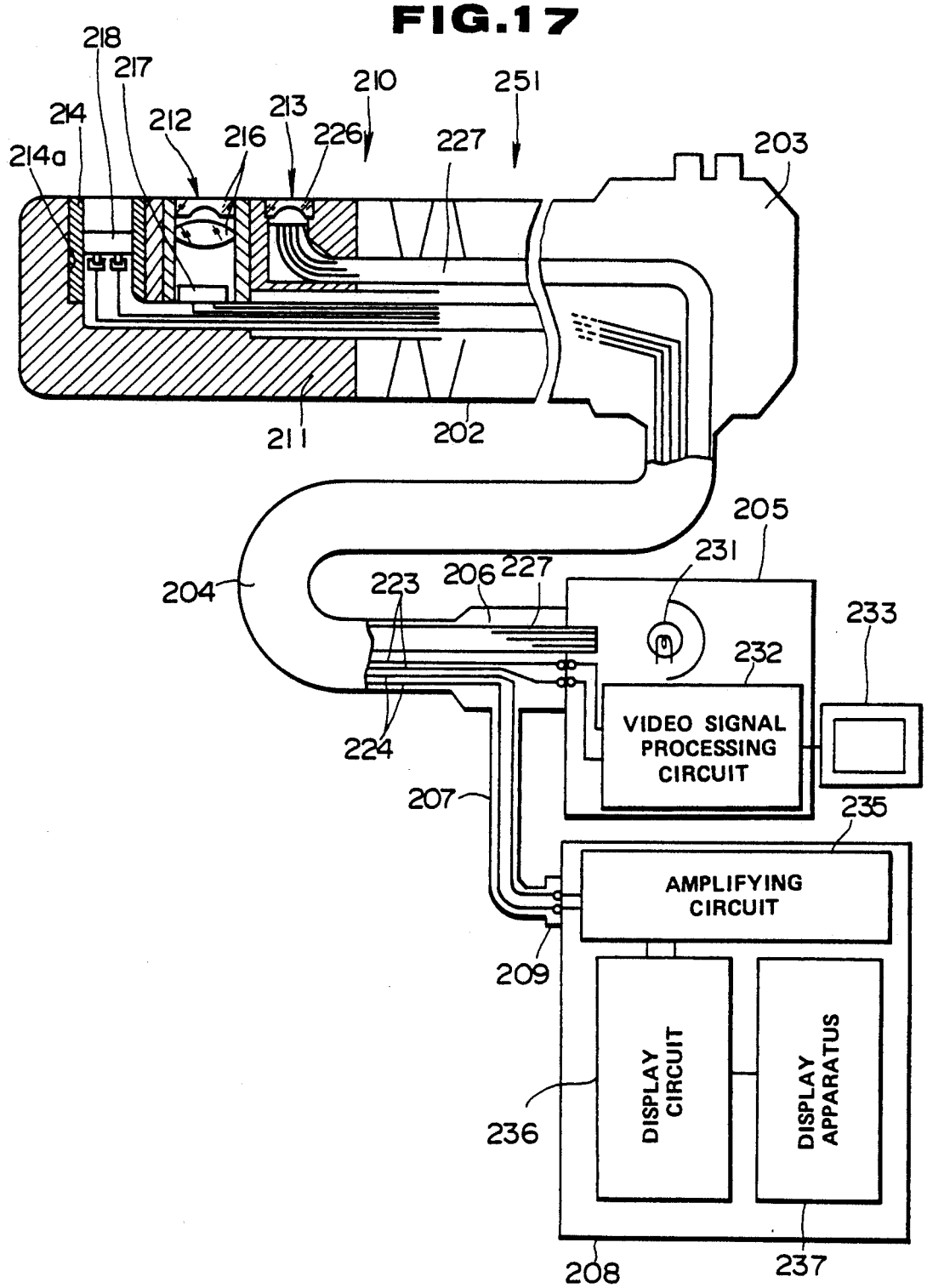

The 11th embodiment of the present invention is shown in FIGS. 17 to 19.

In an endoscope 251 in this embodiment, as shown in FIG. 17, the tip part 210 of an insertable part 202 is provided with a rigid tip body 211 on one side of which are provided a detecting device aperture 214a, observing window 212 and illuminating window 213 in the mentioned order from the tip side. A cylindrical collimator 214 made of radioactive ray attenuating material such as lead is fitted inside the above mentioned detecting device aperture 214a and is internally provided with a radioactive ray detecting device 218 within it. An objective lens system 216 and such solid state imaging device 217 as a CCD are fitted inside the observing window 212.

In this embodiment, there is no such means of switching the solid state imaging device 217 and radioactive ray detecting device 218 to each other with the rotating grip or the like as in the eight embodiment and the other formations are the same as in the eighth embodiment.

As shown in FIG. 18, a forceps port 215 is provided on one side of the observing window 212 and illuminating window 213 and an ultrasonic probe 230 is provided on the other side.

The operation of this embodiment shall be explained in the following.

The same as in the eighth embodiment, while an optical image imaged by the solid state imaging device 217 and an ultrasonic image by the ultrasonic probe 230 are being observed, for example, when a part likely to be an affected part is discovered, the device aperture 214a or radioactive ray detecting device 218 will be opposed to the cancer. Then, such radioactive rays as γ rays emitted from this cancer will reach the above mentioned radioactive ray detecting device 218 and will be detected by this radioactive ray detecting device and the intensity or the like of the radioactive rays detected by this radioactive ray detecting device 218 will be displayed on the display apparatus 237 or on the monitor 233.

In case the above mentioned radioactive ray detecting device 218 is sensitive not only to radioactive rays but also to light, when the radioactive rays are being detected with the above mentioned radioactive ray detecting device 218, it will be desirable to keep the lamp 231 extinguished.

Thus, according to this embodiment, the observation of the optical image and ultrasonic image of the observed part and the detection of the radioactive rays from this observed part can be simultaneously made with the endoscope 251. Therefore, the observed image and radioactive ray generating source can be easily made to correspond to each other and the presence or absence and position of a deep part cancer or lymphatic knot transfer can be easily confirmed.

Further, as the radioactive ray detecting device 218 is provided on the same side surface as of the observing window of the side view type endoscope the radioactive ray detecting device 218 can be easily opposed to a small diameter tubular body cavity wall within which the curvable part can not be curved in the detection.

The eleventh embodiment has been explained on the electronic endoscope as an example but can be applied naturally also to a fiber scope.

FIG. 19 shows a modification of the 11th embodiment and is a schematic view showing a tip part of an endoscope. In this embodiment, a device aperture 214a provided in the tip part 210 of an insertable part 202 is arranged in the rear of an observing window 212, illuminating window 213, forceps port 215 and ultrasonic probe 230.

The 12th embodiment of the present invention is shown in FIGS. 20 to 22.

In this embodiment, as shown in FIG. 20, a radioactive ray detecting device 218 arranged in a detecting device aperture 214a is fitted removably with a fixing screw 261. The other formations and operations are the same as in the 11th embodiment.

In a modification shown in FIG. 21, a radioactive ray detecting device 218 is tapered at the tip and is rather projected out of the tip part 210 on the side. In a modification shown in FIG. 22, for example, a ring-like formed radioactive ray detecting device 262 is removably screwed with a fixing screw 263 to the tip part 210 on the outer periphery.

Figure 23:
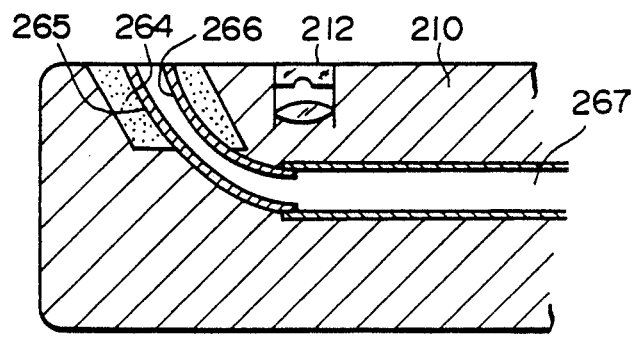
FIGS. 23 and 24 relate to the 13th embodiment of the present invention.
Figure 24:
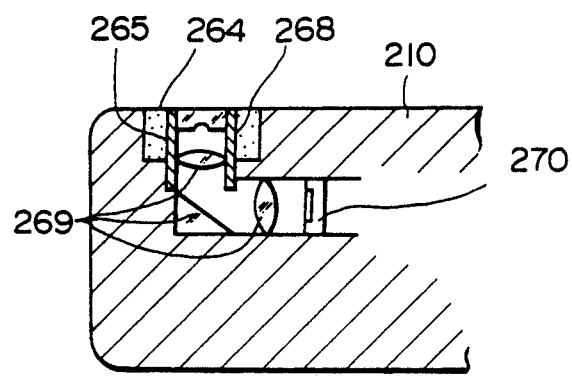

The 13th embodiment of the present invention is shown in FIGS. 23 and 24.

In this embodiment, such component parts as an observing window, illuminating window and forceps channel arranged and formed on the side of the tip part 210 are provided in a hollow part of a ring-like formed radioactive ray detecting device.

In FIG. 23, a forceps pipe 266 is inserted through a hollow part 265 of a ring-like radioactive ray detecting device 264 and is connected to a forceps channel 267. In this embodiment, an affected part detected by the radioactive ray detecting device 264 can be accurately shot with a treating tool concentrically projected out of the center of the above mentioned detecting device 264.

In FIG. 24, a frame 268 is inserted into a hollow part 265 of the above mentioned ring-like radioactive ray detecting device 264 and is provided with an objective lens system 269 within it and a CCD 270 is provide in the image forming position of the objective lens system 269.

The other formations, operations and effects are the same as in the 11th embodiment.

Figure 25:
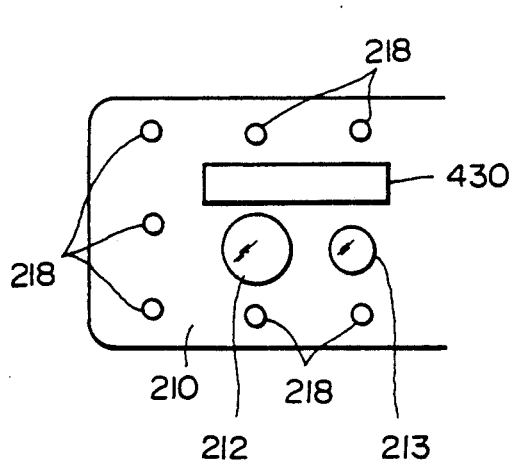
FIGS. 25 and 26 relate to the 14th embodiment of the present invention.
Figure 26:
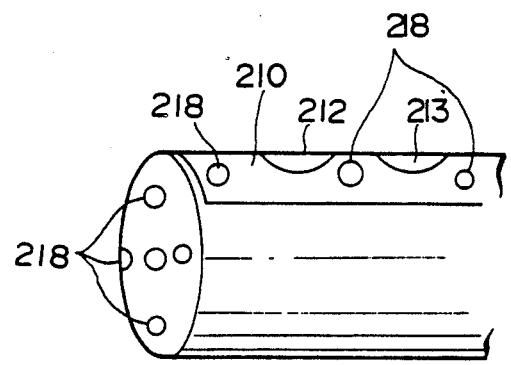

The 14th embodiment of the present invention is shown in FIGS. 25 and 26.

In this embodiment, two or more radioactive ray detecting devices 218 are arranged and not only the intensity of radioactive rays but also the radioactive ray generating source, that is, the position of the affected part can be detected and displayed.

A radioactive ray detecting devices 218 are arranged only on the sides of the tip part 210 in FIG. 25 and are arranged on the sides and tip surface of the tip part 210 in FIG. 26.

According to this embodiment, the position of the radioactive ray generating source can be detected from the ratio of the outputs of the respective radioactive ray detecting devices 218

The 15th embodiment of the present invention is shown in FIGS. 27 to 29.

The radioactive ray detecting device 218 is so low in the directivity that, unless it is brought close to a cancer, the position of the cancer will not be accurately known. Therefore, in this embodiment, as shown in FIG. 27, a cylindrical collimator 271 is internally provided within it with a radioactive ray detecting device 218, is retractably arranged in a device aperture 214a so as to be variable in the effective length, is formed of lead or titanium coated on the surface with a plastic and is projected and retracted by being pushed and pulled with a wire 272 extended through the insertable part from the operating part on the base side or by an energizing means made of a form memorizing alloy or a resin.

FIG. 28 is a perspective view showing another example of a collimator.

The detecting device is so low in the directivity as mentioned above that, in this example, two or more tubular collimators are parallelly arranged to form cellular collimators to improve the directivity. In the example shown in FIG. 28, a plurality of collimators 273 each sectioned like a matrix in the interior are arranged in front of a detecting device 218. In this example, such radioactive rays as γ rays entering at an angle will be absorbed by the inside walls of the respective cells 274 and only the radioactive rays entering at a shallow angle will reach the inner detecting device 218. As a result, the reaction on the front surface of the radioactive ray generating source will be the largest and the location will be able to be specified.

By adjusting the aperture area of one cell 274 of the collimator 273 and the distance from the aperture end to the detecting device 218, the detectable range can be varied.

Further, the cells 274 of the collimator 273 may be formed, for example, as shown in FIGS. 29(A) to (D).

That is to say, shown in FIG. 29(A) are rectangular cross-sections of the cells 274, shown in FIG. 29(B) are hexagonal cross-sections of the cells 274, shown in FIG. 29(C) is a circular cross-sections of the cells 274 and shown in FIG. 29(D) are diamond-shaped cross-sections of the cells 274.

Figure 30:
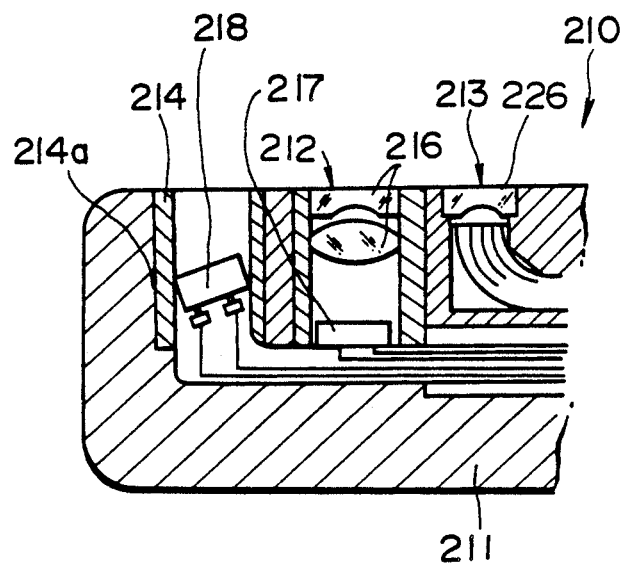
FIG. 30 is a sectioned view of an essential part of an endoscope in the 16th embodiment of the present invention.

The 16th embodiment of the apparatus of the present invention is shown in FIG. 30.

In this embodiment, a radioactive ray detecting device 218 arranged within a collimator 214 is obliquely arranged. According to this embodiment, the area of the device 218 will be large against the aperture of the collimator 214 and the detecting efficiency will be high.

The other formations, operations and effects are the same as in the 11th embodiment.

Figure 31:
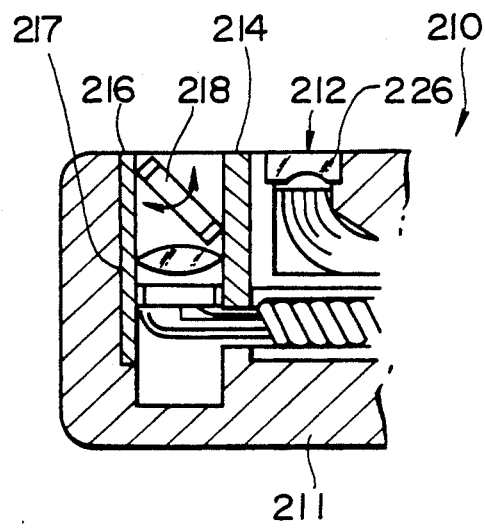
FIG. 31 is a sectioned view of an essential part of a tip part of an endoscope in the 17th embodiment of the present invention.

The 17th embodiment of the present invention is shown in FIG. 31.

In this embodiment, an objective optical system 216 and, for example, a CCD 217 are arranged in the rear of a radioactive ray detecting device 218 within a collimator 214 and the detecting device 218 positioned in front of these observing systems is formed to be retractable. In the illustrated example, the detecting device 218 is arranged to be retractable into the collimator 214 so that, in the case of the detection, the detecting device 218 will obliquely rise to be opposed to the aperture of the collimator 214 but, in the case of the observation, the detecting device will fall, the objective lens 216 will be opposed to the aperture of the collimator 214 and the reflected light from the object will enter. Various known techniques can be utilized for the means of setting and retreating the detecting device 218. For example, the detecting device may be rotated with a spring made of a form memorizing alloy or a resin or, by a combination of a wire and spring, the detecting device 218 will be retreated with the spring at the normal time but will be pulled and set against the spring as required.

The other formations, operations and effects are the same as in the 11th embodiment.

Figure 32:
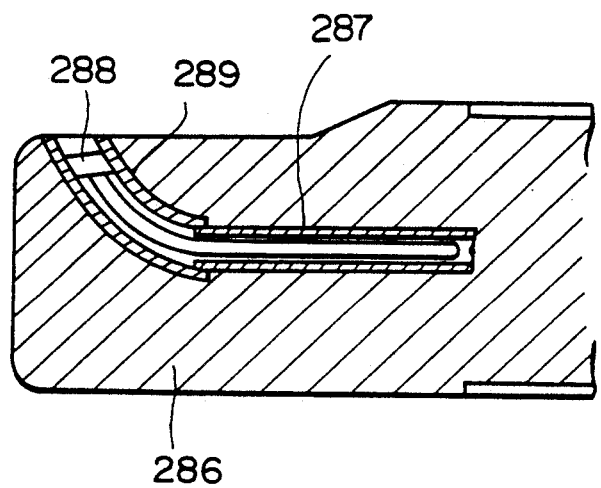
FIGS. 32 and 33 relate to the 18th embodiment of the present invention.
Figure 33:
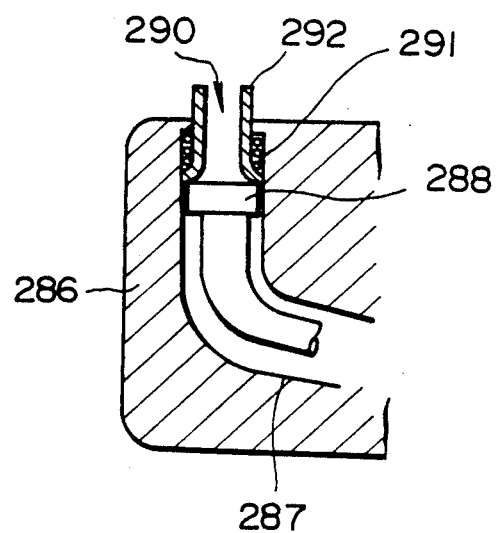

The 18th embodiment of the present invention is shown in FIGS. 32 and 33.

In this embodiment, a detecting probe 288 is arranged by using a forceps channel 287 without arranging the radioactive ray detecting device directly within the tip part of the insertable part. As shown in FIG. 32, the part of the foreceps channel 287 provided in the tip part 286 or particularly the forceps port part reached by the radioactive ray detecting probe 288 is formed of a cylindrical collimator 289 made of such radioactive ray attenuating material as lead or tungsten. As shown in FIG. 33, a collimator 292 normally energized in the retreating direction with a spring 291 is arranged in a forceps port 290 so that, in the case of the detection, when the radioactive ray detecting probe 288 comes to the position of the collimator 292, this collimator 292 will be projected against the spring 291 as illustrated.

The other formations, operations and effects are the same as in the 11th embodiment.

The 19th embodiment of the present invention is shown in FIGS. 34 to 41.

Figure 34:
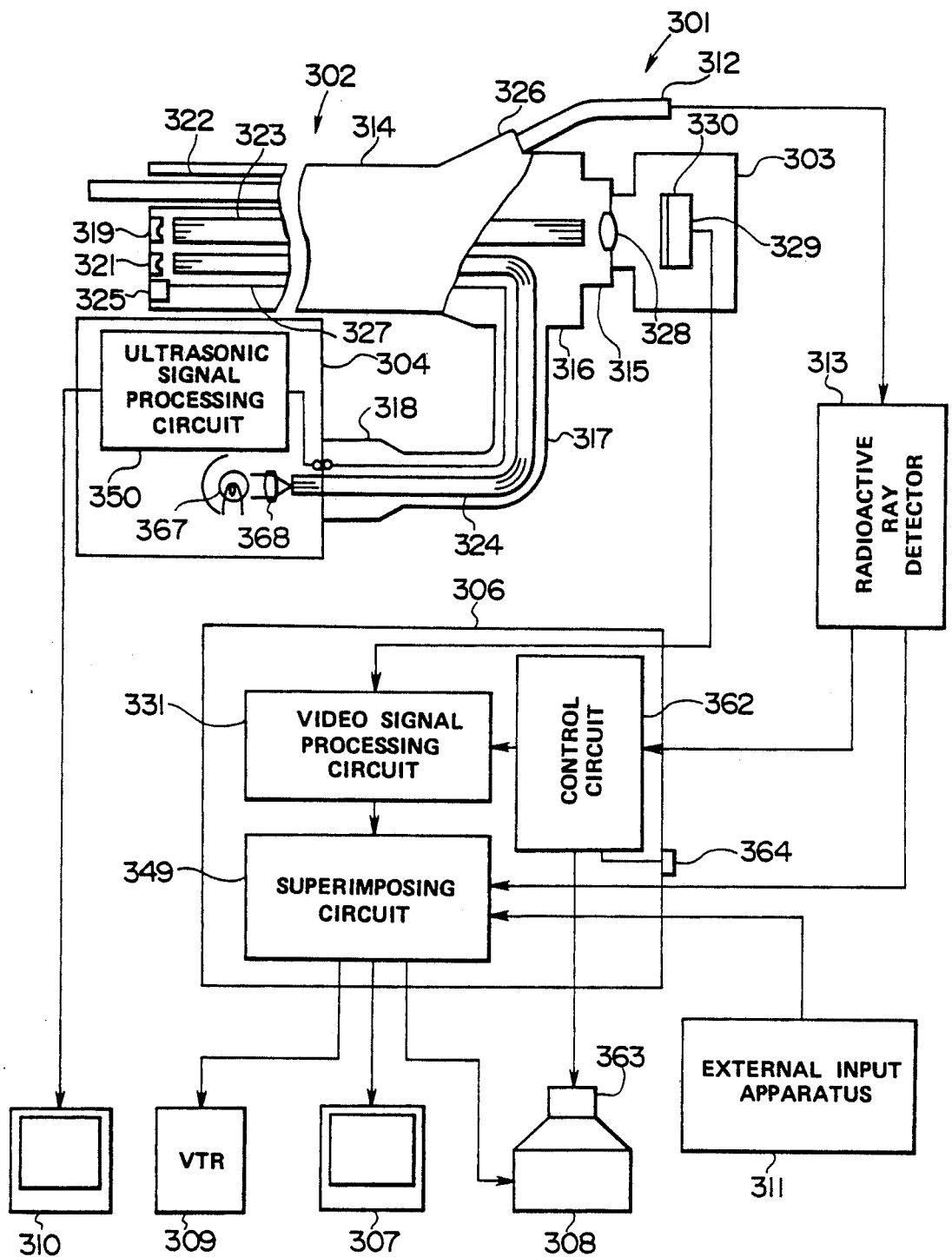

As shown in FIG. 34, a radioactive ray detecting endoscope apparatus 301 comprises an ultrasonic endoscope 302, an externally fitted TV camera 303 removably fitted to this ultrasonic endoscope 302, an ultrasonic observing apparatus 304 feeding an illuminating light to the above mentioned ultrasonic endoscope 302 and processing signals for an ultrasonic probe, a camera controlling unit (which shall be abbreviated as CCU hereinafter) 306 processing the output signal of the above mentioned externally fitted TV camera 303, a monitor 307 connected to this CCU 306, a picture imaging apparatus 308, a video tape recorder (abbreviated as VTR hereinafter) 309, an external input apparatus 311 connected to the above mentioned CCU 306, a radioactive ray detecting probe 312 as a radioactive ray detecting means inserted through the above mentioned ultrasonic endoscope 302, a radioactive ray detector 313 connected to this radioactive ray detecting probe 312 and a monitor 310 connected to the above mentioned ultrasonic observing apparatus 304.

In the above mentioned ultrasonic endoscope 302, an operating part 316 is connected to an elongated insertable part 314 in the rear part and an eyepiece part 315 to which the above mentioned externally fitted TV camera 303 is provided at the rear end of this operating part 316. A universal cable 317 is extended out of the side of the above mentioned operating part 316 and is provided at the rear end with a connector 318 connected to the above mentioned ultrasonic observing apparatus 304.

The ultrasonic observing apparatus 304 has a light source lamp 367 so that the illuminating light emitted from this light source apparatus will be condensed by a condenser lens 368 and will be radiated to the entrance end surface of a light guide fiber 324 formed of a fiber bundle inserted through the above mentioned universal cable 317.

The above mentioned insertable part 314 is provided in the tip part with an objective lens system 319, a light distributing lens system 321, an aperture of a treating tool channel 322 inserted through the insertable part 314 and an ultrasonic probe 325. The entrance end surface of an image guide fiber 323 formed of a fiber bundle is provided in the image forming position of the above mentioned objective lens system 319. The exit end surface of the above mentioned light guide fiber 324 is provided in the rear of the light distributing lens system 321.

Within the above mentioned treating tool channel 322, an elongated radioactive ray detecting probe 312 is inserted through an inserting port 326 provided on the side of the operating part 316.

A signal line 327 is connected to the above mentioned ultrasonic probe 325, is inserted through the insertable part 314, operating part 316 and universal cable 317, is connected to a connector 318 and is connected through this connector 318 to an ultrasonic signal processing circuit 350 within the ultrasonic observing apparatus 304.

Figure 35:
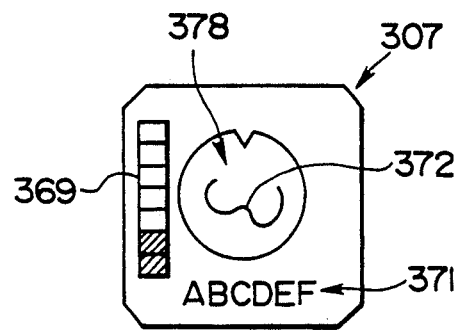

The exit end surface of the above mentioned image guide fiber 323 is provided to face an eyepiece lens 328 by which an object image 378 as shown in FIG. 35, will be formed on the imaging surface of such solid state imaging device as, for example, a CCD 329 provided in the externally fitted TV camera 303. A mosaic-like color filter 330 transmitting respective color light of red (R), green (G) and blue (B) is pasted to the imaging surface of this CCD 329.

The above mentioned CCD 329 will photoelectrically convert the object image 378 and the obtained electric signal will be read out by a driving clock applied from a CCD driver (not illustrated) and will be output in a video signal processing circuit 331 provided in the CCU 306.

Figure 36:
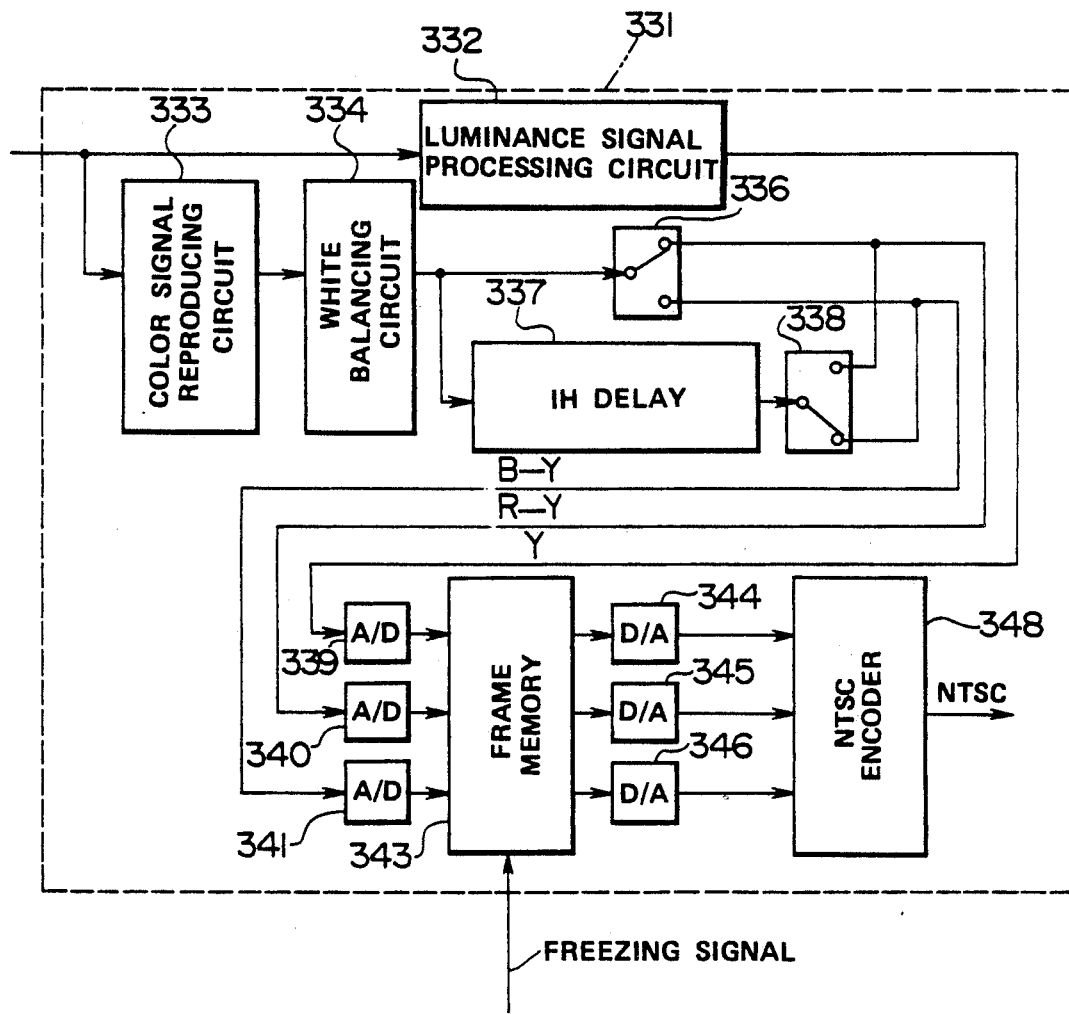

As shown in FIG. 36, the output of the CCD 329 will be input into a luminance signal processing circuit 332 and color signal reproducing circuit 333 within the video signal processing circuit 331. A luminance signal Y will be produced from the luminance signal processing circuit 332. Color difference signals R-Y and B-Y will be produced from the color signal reproducing circuit 333 in time series per horizontal line and will be compensated with a white balance in a white balancing circuit 334. The output of this white balancing circuit 334 will be branched. One branch will be input into an analogue switch 336 and the other will be input into an analogue switch 338 as delayed by 1 horizontal line by a 1H delay circuit 337. The analogue switches 336 and 338 will be switched by a switching signal of a timing generator (not illustrated) to produce color difference signals R-Y and B-Y. The above mentioned luminance signal Y and color difference signals R-Y and B-Y will be converted to digital signals respectively by A/D converters 339, 340 and 341 and then will be stored in a frame memory 343. The signals stored in this frame memory 343 will be read out, for example, in the lateral direction at a velocity synchronized with the monitor 307, will be converted to analogue signals respectively by D/A converters 344, 345 and 346, will be multiplexed by an NTSC encoder 348 and will be output, for example, as an NTSC video signal.

As shown in FIG. 34, the NTSC video signal will be input into a superimposing circuit 349 and the NTSC video signal having passed through the superimposing circuit 349 will be output to the monitor 307 and will display an object image 378 (FIG. 35) on a picture surface. Further, the NTSC video signal will be output to a VTR 309 and a monitor not illustrated provided in a picture image imaging apparatus 308.

An external input apparatus 311 as, for example, a keyboard is further connected to the above mentioned superimposing circuit 349 so that the data of the patient and the resistor information (such as the resistor name, mixing ratio and administration amount) used in the inspection may be input by the inspector so as to be superimposed on the NTSC video signal.

Figure 37:
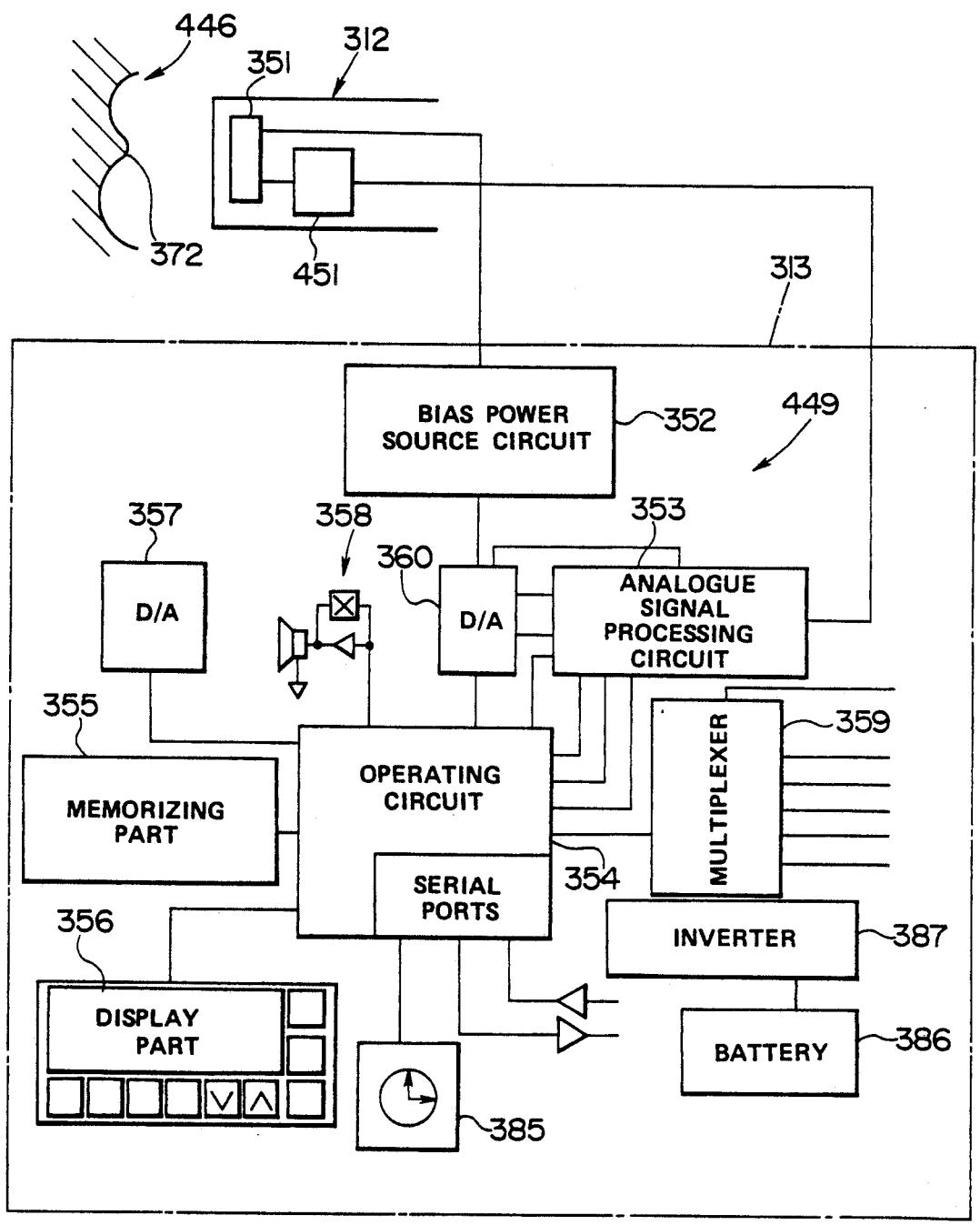

On the other hand, the radioactive ray detecting probe 312 inserted through the treating tool channel 322 of the above mentioned insertable part 314 and the radioactive ray detector 313 are formed as shown, for example, in FIG. 37.

The above mentioned elongated radioactive ray detecting probe 312 is provided in the tip part with a radioactive ray detecting sensor 351 which can detect radioactive rays. This radioactive ray detecting sensor 351 is fed with a bias power by a bias power source circuit 352 provided in a radioactive ray detecting circuit 449 forming the radioactive ray detector 313. When this radioactive ray detecting sensor 351 detects radioactive rays, a signal will be output, will be input into an amplifier 451 provided near the radioactive ray detecting sensor 351 to improve the S/N of this signal, will be amplified by the amplifier 451, will be input into an analogue signal processing circuit 353 provided in a radioactive ray detecting circuit 449, will be processed by the analogue signal processing circuit 353 so as to be an information signal relating to the intensity of the radioactive rays and will be output to the operating circuit 354. A gain control signal will be input into the analogue signal processing circuit 353 from the D/A converter 360 outputting a control signal to the above mentioned bias power source circuit 352.

In the above mentioned operating circuit 354, a character code corresponding to the input signal will be selected out of a memorizing part 355 as, for example, an EPROM and will be output to a display part 356 as, for example, a liquid crystal panel to display the intensity of the radioactive rays. At the same time, when radioactive rays are detected by the operating circuit 354, a speaker 358 will be sounded intermittently to inform the inspector of the detection of radioactive rays.

The above mentioned operating circuit 354 can output the radioactive ray intensity to the apparatus through an outside output D/A converter 357. The operating circuit 354 can control the apparatus by an analogue 8-channel multiplexer 359.

A timer clock 385 is provided within the radioactive ray detecting circuit 449 so as to deliver a clock signal to the operating circuit 354.

A battery 386 and inverter 387 are provided within the radioactive ray detecting circuit 449 so as to be able to feed power, for example, of 12V.

The D/A converter 357 received in the above mentioned radioactive ray detector 313 will output the intensity of radioactive rays to the above mentioned superimposing circuit 349 in which the radioactive ray intensity information will be superimposed on the NTSC video signal and picture image as is shown in FIG. 35 will be displayed on the picture surface of the monitor 307. In FIG. 35, the bar graph 369 will move upward when the intensity of radioactive rays is high but downward when it is low. The resistor information 371 will be input from the above mentioned external input apparatus 311.

When the measured intensity becomes higher than the preset intensity, the operating circuit 354 of the radioactive ray detector 313 will issue a trigger signal and will input it into a control circuit 362 provided in the CCU 306. When the trigger signal is input into the control circuit 362, a freezing signal will be output in the above mentioned frame memory 343, writing in a video signal will be prohibited and the picture image in the monitor 307 and the picture in the monitor provided in the picture image imaging apparatus 308 will be still picture images. After the writing in prohibiting signal is output, a releasing signal will be output to a still camera 363 which can image the picture image in a monitor (not illustrated) provided in the picture imaging apparatus 308 and the object image 378 on the monitor picture surface will be photographed by the still camera 363. An on-off signal can be input into the control circuit 362 by a manual switch 364. When an on-signal is input from this switch 364, a control signal releasing the writing-in prohibition will be output to the frame memory 343 by the control circuit 362.

By the ultrasonic signal processing circuit 350 within the above mentioned ultrasonic observing apparatus 304, a transmitting pulse will be transmitted to the ultrasonic probe 325 through the signal line 327 and the output signal of this ultrasonic probe 325 will be processed. The video signal output from this ultrasonic signal processing circuit 350 will be input into the monitor 310 and the ultrasonic image of the observed part will be displayed in this monitor 310.

The operation of the radioactive ray detecting endoscope apparatus 301 formed as in the above shall be explained.

In case a cancer is to be inspected by using the radioactive ray detecting endoscope apparatus 301 of this embodiment, at a predetermined time before the inspection, a cancer resistor marked with a radio-isotope or a deoxyglucose likely to concentrate on a cancer will be injected into the body by venous injection or the like. Such a reagent will concentrate on the cancer and radioactive rays as, for example, γ rays will be emitted from this cancer.

Then, the ultrasonic endoscope 302 wherein the radioactive ray detecting probe 312 is inserted through the treating tool channel 322 will be inserted into the body cavity.

The illuminating light emitted from the light source lamp 367 provided in the ultrasonic observing apparatus 304 will be condensed by the condenser lens 368, will be radiated to the entrance end surface of the light guide fiber 324, will be transmitted through the light guide fiber 324 and will illuminate the object 446 by the light distributing lens system from the exit end surface of the light guide fiber 324. This illuminated object 446 will form an image on the entrance end surface of the image guide fiber 323 by the objective lens system 319. The object image will be transmitted through this image guide fiber 323 and will be formed on the imaging surface of the CCD 329 of the externally fitted TV camera 303 by the eyepiece lens 328. This formed optical image will be converted to an electric signal by photoelectric conversion. This electric signal will be read out by a driving clock applied by a CCD driver (not illustrated) will be input into the video signal processing circuit 331 within the CCU 306 and will be converted, for example, to an NTSC video signal. This NTSC video signal will have the patient data input from the external input apparatus 311 by the superimposing circuit 349 and the resistor information used for the inspection superimposed and will be output to the monitor 307. On the picture surface of the monitor 307, a bar graph 369 showing the intensity of the radioactive rays and resistor information 371 as are shown in FIG. 35 will be displayed. The resistor information 371 will be input in advance in the external input apparatus 311.

When an ultrasonic image of a living body tissue is to be observed, a transmitting pulse will be transmitted to the ultrasonic probe 325 from the ultrasonic signal processing circuit 350 within the ultrasonic observing apparatus 304 and an ultrasonic pulse will be emitted toward the living body tissue from this ultrasonic probe 325. An echo from the living body tissue by the ultrasonic pulse will be received and converted to an electric signal by the above mentioned ultrasonic probe 325. The output signal of this ultrasonic probe 325 will be processed by the ultrasonic signal processing circuit 350. The video signal output from this ultrasonic signal processing circuit 350 will be input into the monitor 310 and the ultrasonic image of the observed part will be displayed in this monitor 310.

When the insertable part 314 is inserted into the body cavity and the radioactive rays emitted from the cancer 372 are detected by the radioactive ray detecting probe 312, the bar graph 369 will gradually rise. When the intensity of the radioactive rays further rises and reaches a preset radioactive ray intensity, a trigger signal will be generated by the radioactive ray detector 313 and will be output to the control circuit 362. A freezing signal will be output to the frame memory 343 from the control circuit 362 and a new video signal will be prohibited from being written in. When the writing in is prohibited, the monitor picture images in the monitor 307 and the monitor (not illustrated) contained in the picture image photographing apparatus 308 will become still picture images. After the freezing signal is output from the control circuit 362, a releasing signal will be output to the still camera 363 provided in the picture imaging apparatus 308 to photograph a still picture image. After the photographing ends, the manual switch 364 will be switched on by the operator to output a writing-in prohibition releasing signal to the frame memory 343 from the control circuit 362. When the writing in prohibition releasing signal is input into the frame memory 343, the writing-in will be resumed and the picture images in the monitor 307 and the monitor (not illustrated) provided in the picture imaging apparatus 308 will be returned to moving pictures.

A video signal superimposed with the intensity of the radioactive rays will be output to the VTR 309 from the superimposing circuit 349 so that, when the VTR 309 is operated by the inspector, a desired picture image may be recorded on a magnetic tape or the like.

Thus, according to this embodiment, as the intensity of radioactive rays is superimposed on the video signal by the superimposing circuit 349, the intensity of the radioactive rays together with the object image 378 can be visionally observed by the inspector and therefore a quick diagnosis can be made.

When the intensity of the radioactive rays becomes higher than the preset intensity, a trigger signal will be generated from the radioactive ray detector 313 so that the object image 378 may be automatically photographed. Therefore, the picture imaging apparatus 308 need not be operated to be released by the inspector and the operatability is high.

The tip part 376 (FIG. 38) provided with the radioactive ray detecting sensor 351 of the radioactive ray detecting probe 312 may be made rotatable so that the radioactive ray in the direction diametral to the lengthwise direction of the probe 312 may be detected. In such a case, in order to elevate the directivity of the radioactive ray detecting sensor 351, as shown in FIG. 40(A), the radioactive ray detecting sensor 351 may be provided on a shielding plate 377 formed of a radioactive ray attenuable material and provided rotatably at the lengthwise direction center of the probe 312 so as to shield the radioactive rays coming from the back surface of the radioactive ray detecting sensor 351. Also, as in FIG. 40(B), radioactive ray detecting sensors 351 may be provided on both surfaces of the shielding plate 377 so that the radioactive rays in two directions may be simultaneously detected.

The measuring results obtained by the radioactive ray detecting probe 312 shown in FIG. 38 may be displayed as in FIG. 39. That is to say, in FIG. 39, a displaying part 379 display the intensity of radioactive rays is provided around the object image 378 so that the position corresponding to the cancer 372 of this display part 379 may be, for example, black and the other parts may be white. Therefore, in what direction of the object image 378 the cancer 372 is located can be detected by the thickness of the color of the display part.

Also, in order to elevate the directivity of the radioactive ray detecting sensor 351, as shown in FIG. 41, a probe 383 provided with a radioactive ray detecting sensor 351 may be inserted into a sheath 382 formed to be cylindrical of a radioactive ray attenuable material and having an aperture 381. This sheath 382 is sealed on the periphery and is provided with the above mentioned aperture 381 on the cylindrical surface near the tip. In the detection of radioactive rays, when the sheath 382 is rotated until the position of the aperture 381 corresponds to the cancer 372 emitting radioactive rays. The radioactive rays will enter the sheath 382 through the aperture 381 and will be detected by the radioactive ray detecting sensor 351. Therefore, the part of the cancer 372 can be detected by the position of the aperture 381.

In this embodiment, the intensity of radioactive rays is displayed together with the optical image of the object but may be displayed together with the ultrasonic image or the radioactive ray intensity, optical image and ultrasonic image may be displayed on the same monitor.

Figure 42:
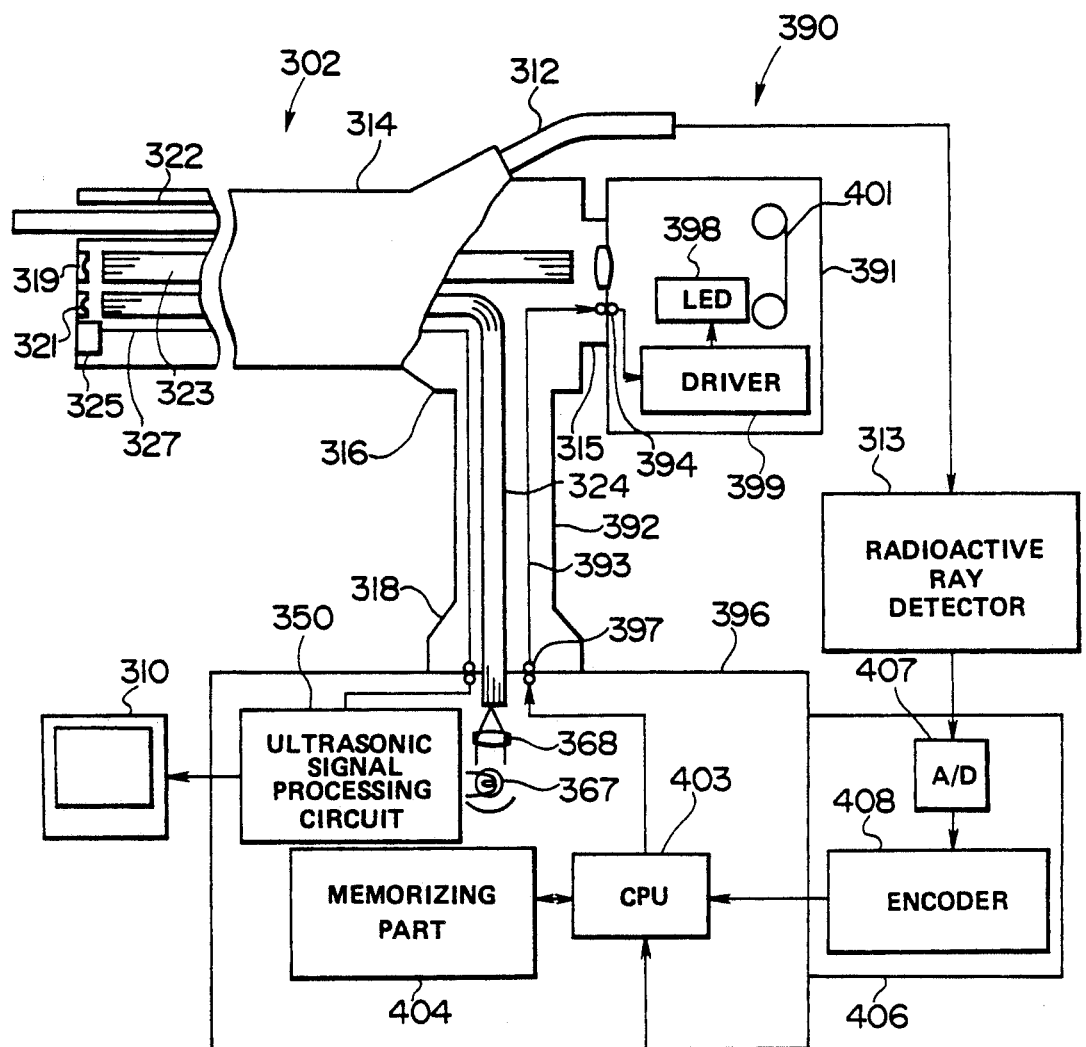
FIGS. 42 and 43 relate to the 20th embodiment of the present invention.
Figure 43:
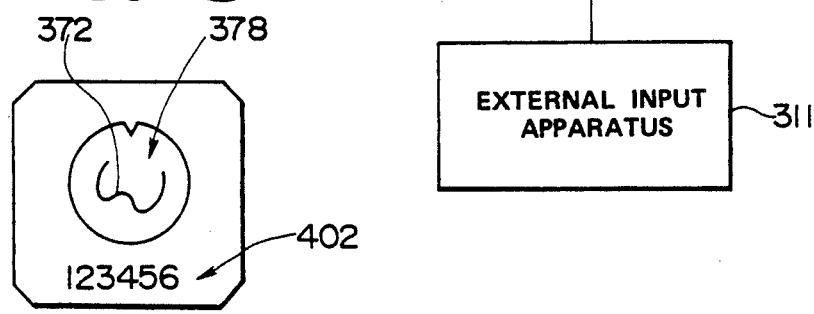

The 20th embodiment of the present invention is shown in FIGS. 42 and 43.

In this embodiment, an externally fitted still camera 391 is fitted to the ultrasonic endoscope 302 of the 19th embodiment.

A light guide fiber 324 feeding an illuminating light to the ultrasonic endoscope 302 and signal lines 393 and 327 are inserted through a universal cable 392 extended to an operating part 316 of the ultrasonic endoscope 302 forming a radioactive ray detecting endoscope apparatus 390. This signal line 393 is connected at one end to a contact 394 provided on an eyepiece part 315 and at the other end to a contact 397 provided on a CCU 396 having a light source part and signal processing part. The other formations of the ultrasonic endoscope 302 are the same as in the 19th embodiment.

The externally fitted still camera 391 is removably fitted to the above mentioned eyepiece part 315. The above mentioned contact 394 is connected to a driver 399 driving a 7-segment LED 398 as a display means. In this 7-segment LED 398, in case an object image 378 obtained with the ultrasonic endoscope 302 is to be photographed with a photographing film 401, as shown in FIG. 43, such photographing data 402 relating to the object image 378 as the data of the patient and the resistor information (for example, the resistor name, mixing ratio and administration amount) used in the inspection will be lighted and displayed so as to be able to be recorded together with the object image 378 on the photographing film. These photographing data 402 will be output from a CPU 403 connected to the contact 397 through the above mentioned signal line 393. This CPU 403 is connected to an external input apparatus 311 as, for example, a keyboard. A character code corresponding to the data code input from this outside input apparatus 311 will be selected out of a memorizing part 404 and will be output to the driver 399.

The radioactive ray detecting probe 312 as a radioactive ray detecting means inserted through the treating tool channel 322 of the above mentioned ultrasonic endoscope 302 is connected to a radioactive ray connector 313 which can detect the radioactive rays in the object part. This radioactive ray detector 313 will input the measured intensity information of the radioactive rays into an A/D converter 407 within an expansion box 406 connected to the CCU 396. The A/D converter 407 will output the intensity information of the radioactive rays as a digital signal to an encoder 408 which is connected so as to be able to encode and input the signal into the CPU 403. When the expansion box 406 is connected and data are input from the encoder 408, the CPU 403 will prohibit the input from the outside input apparatus 311 and will output the data from the encoder 408 to the driver 399. The operation of the radioactive ray detecting endoscope apparatus 390 formed as in the above shall be explained.

In case the expansion box 406 of the radioactive ray detector 313 is not connected to the CCU 396, the CPU 403 will be able to input the data from the external input apparatus 311. Therefore, the data input from the external input apparatus 311 will be input into the CPU 403 which will select a character code corresponding to these data from the memorizing part 404 and will deliver it to the driver 399 of the externally fitted still camera 391 through the signal line 393. The driver 399 will drive the 7-segment LED 398, will display the data of the patient and the resistor information used in the inspection as photographing data 402 as shown in FIG. 43 and will photograph them together with the object image 378 with photographing film 401.

In the case of the endoscope observation and radioactive ray detection, the radioactive ray detecting probe 312 will be inserted through the treating tool channel 322 and the expansion box 406 will be connected to the CCU 396. When the expansion box 406 is connected to the CCU 396, the CPU 406 will prohibit the input of the data from the external input apparatus 311 so that the data from the encoder 408 may be input.

When the detection with the radioactive ray detecting probe 312 is started and the cancer 372 is approached, the radioactive ray detector 313 will detect radioactive rays, will compute the intensity of the radioactive rays and will output the data to the expanding box 406. The data will be digitalized by the A/D converter 406 and will be encoded by the encoder 408. As the CPU 403 can input the data of the radioactive ray intensity from the encoder 408, it will input the encoded data and will further output them to the driver 399 of the externally fitted still camera 391. The driven 399 will output the data of the radioactive ray intensity to the 7-segment LED 398 which will light the data of the radioactive ray intensity. The inspector can observe the object image 378 from a finder or the like (not illustrated) can know the intensity of the radioactive rays of the object image 378 and can further photograph this object image 378 and the intensity of the radioactive rays on the photographing film 401.

Thus, according to this embodiment, the endoscope image and the intensity of the radioactive rays of this endoscope image can be simultaneously known and can be photographed and recorded as data.

The formations, operations and effects are the same as in the 19th embodiment.

Figure 44:
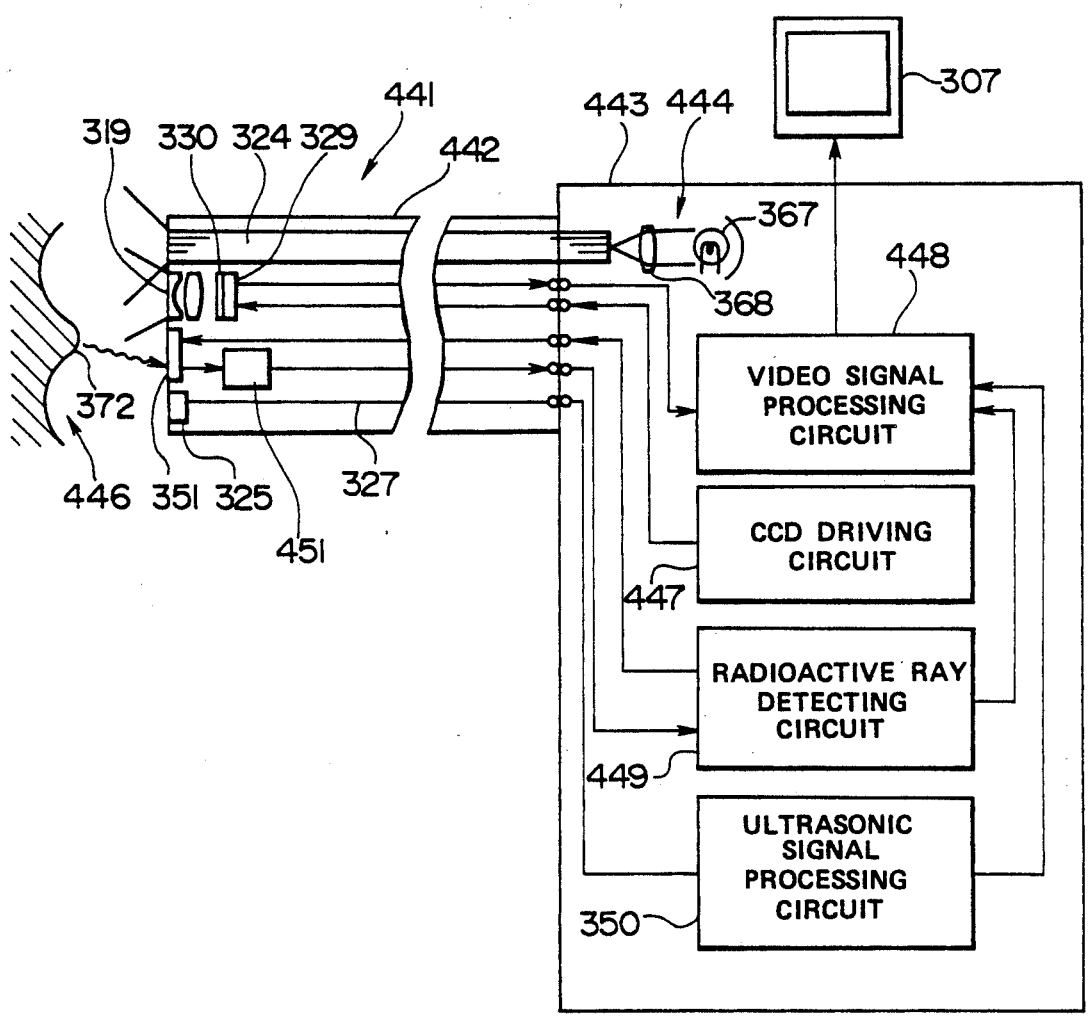
FIG. 44 is an explanatory view showing the formation of an endoscope apparatus in the 21st embodiment of the present invention.

The 21st embodiment of the present invention is shown in FIG. 44.

In this embodiment, an electronic scope 441 is provided with a radioactive ray detecting sensor 351.

In FIG. 44, an elongated insertable part 442 of the electronic scope 441 is provided in the tip part with an objective lens system 319, an exit end surface of a light guide fiber 324, a radioactive ray detecting sensor 351 and an ultrasonic probe 325. The light guide fiber 324 inserted through the insertable part 442 will be fed with an illuminating light from a light source part 444 provided within a control apparatus 443 connected to the electronic scope 441. This light source part 444 has a light source lamp 367 emitting an illuminating light. The illuminating light emitted from this light source lamp 367 will be condensed by a condenser lens 368 and will be radiated to the entrance end surface of the light guide fiber 324. An object image 378 radiated by the illuminating light will be formed on the imaging surface of a CCD 329 provided in the image forming position of the objective lens system 319. A mosaic-like color filter 330 transmitting the respective colors of red (R), blue (B) and green (G) is pasted to the imaging surface of the CCD 329. This CD 329 will photoelectrically convert the object image, will read it out as an electric signal when a driving pulse is applied from a CCD driving circuit 447 provided in the control apparatus 443 and will be delivered to a video signal processing circuit 448 within the control apparatus. In this video signal processing circuit 448, an input signal will be converted to a composite video signal, for example, of an NTSC system and will be output to a monitor 307 and the object image 378 will be displayed on the picture surface of the monitor 307.

An ultrasonic signal processing circuit 350 connected to the ultrasonic probe 325 through the signal line 327 is provided within the above mentioned control apparatus 443. The video signal from this ultrasonic signal processing circuit 350 will be input into the monitor 307 through the above mentioned video signal processing circuit 448 and an ultrasonic image will be displayed on this monitor 307.

Further, the radioactive ray detecting sensor 351 at the tip of the insertable part 442 will be fed with a bias power from a radioactive ray detecting circuit 449 provided within the control apparatus 443. When radioactive rays from the cancer 372 of the object 446 enter the radioactive ray detecting sensor 351, a signal will be generated, will be amplified by an amplifier 451 provided near the radioactive ray detecting sensor 351 to improve S/N and will be delivered to the radioactive ray detecting circuit 449. The intensity of the radioactive rays will be computed by the radioactive ray detecting circuit 449 and a signal representing the intensity will be delivered to the video signal processing circuit 448, will be superimposed on a composite video signal by the video signal processing circuit 448 and will be output to the monitor 307 in which the object 446 and the intensity of the radioactive rays of this object 446 will be displayed.

Thus, in this embodiment, as the radioactive ray detecting sensor 351 is contained in the electronic scope 441 whereby even the ultrasonic image can be observed, by only inserting the electronic scope 441 into the body cavity, the observation of the inspected part and the measurement of the intensity of radioactive rays can be simultaneously made. Further, as the object image 378 and the intensity of radioactive rays can be displayed on the picture surface of the monitor 307, the diagnosis can be quickly made and the fatigue of the inspector can be reduced.

Figure 45:
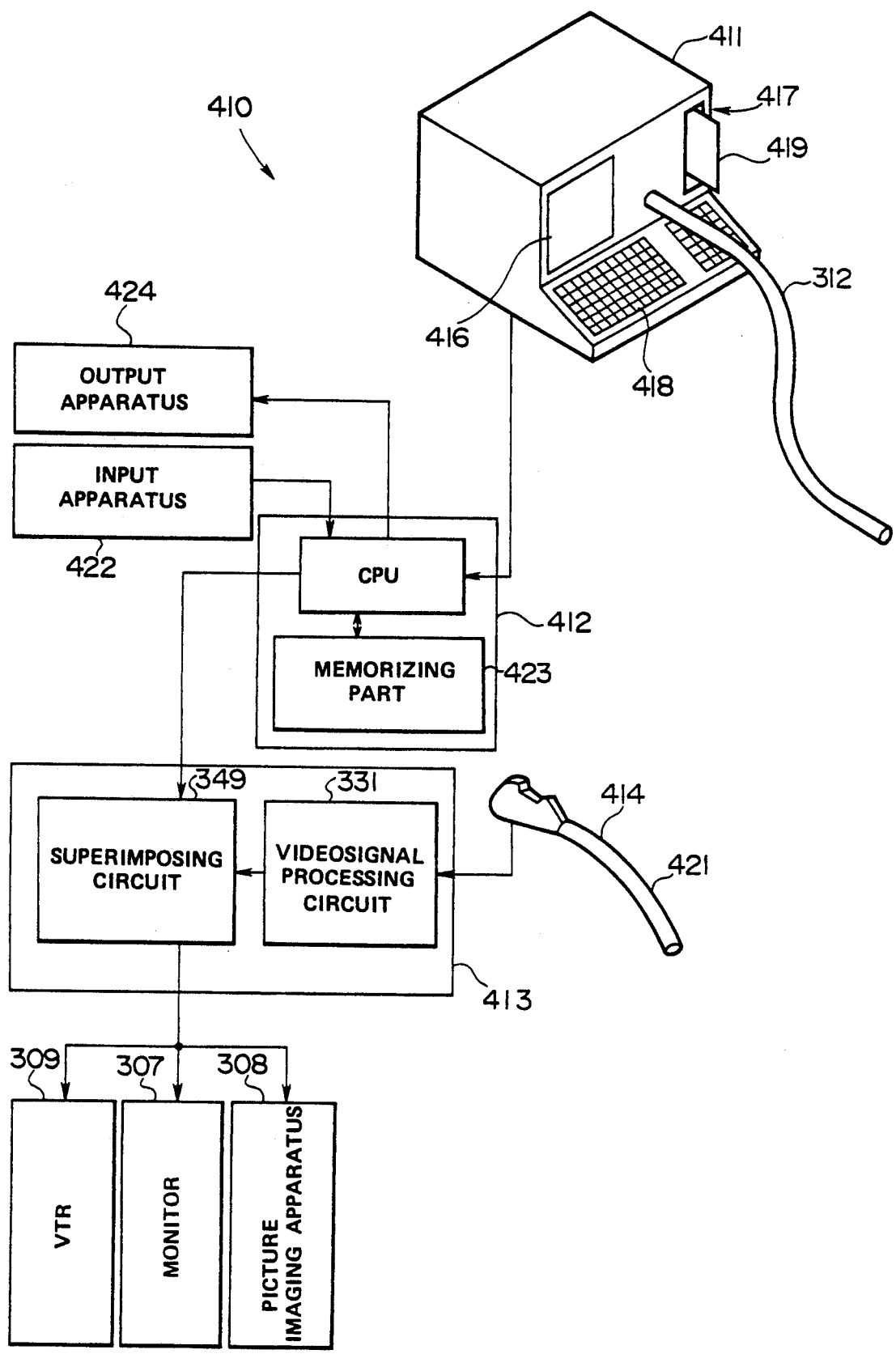
FIGS. 45 and 46 relate to the 22nd embodiment of the present invention.
Figure 46:
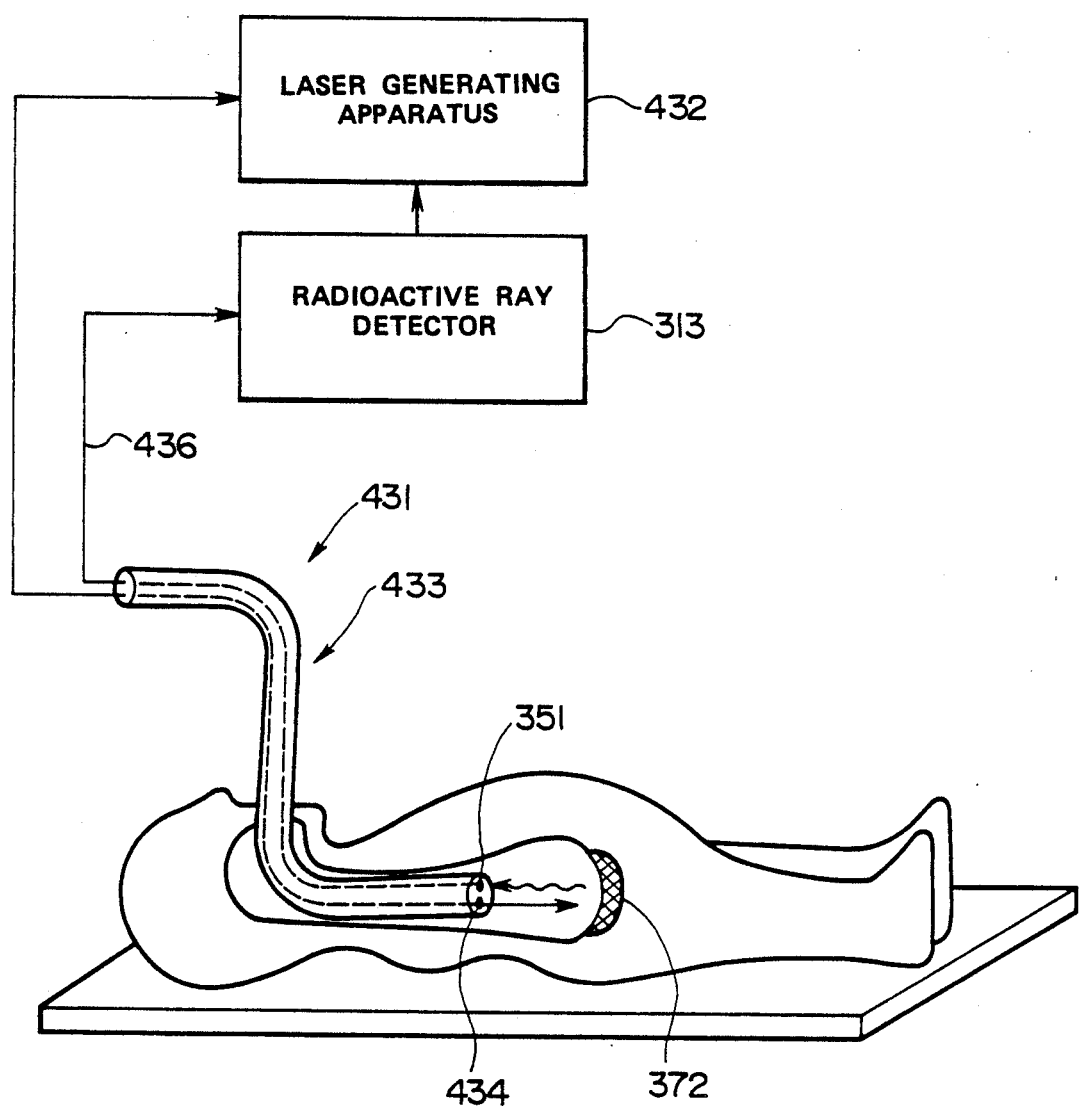

The 22nd embodiment of the present invention is shown in FIG. 45 and 46.

A radioactive ray detecting endoscope 410 of this embodiment comprises a radioactive ray detecting apparatus 411, a personal computer 412 which can take in data detected by this radioactive ray detecting apparatus 411, a CCU 413 into which the data are input from this personal computer, an electronic scope 414 connected to this CCU 413 and delivering to this CCU 413 an electric signal including a video information and a monitor 307, picture image photographing apparatus 308 and VTR 309 connected to this CCU 413.

The above mentioned radioactive ray detecting apparatus 411 comprises a display 416 which can connect a radioactive ray detecting probe 312 and can display data as picture images, a floppy driver 417 storing data and a keyboard 418 as an input means. The intensity of radioactive rays detected by the radioactive ray detecting probe 312 will be displayed on the above mentioned display 416 together with the data of the patient and the resistor information used in the inspection input by a keyboard 418. These displayed data will be stored in a floppy 419 by a flopping driver 417.

On the other hand, the electronic scope 414 is connected to the CCU 413 and will deliver an electric signal obtained by photoelectric conversion from a solid state imaging device as an imaging means (not illustrated) provided in the tip part of an insertable part to a video signal processing circuit 331 within the CCU 413. The electric signal will be converted to a video signal by a video signal processing circuit 331 and the video signal will be output to a superimposing circuit 349 in which the data of the patient input from such input apparatus 422 as, for example, a keyboard connected to the above mentioned personal computer 412 can be superimposed on the video signal. The video signal superimposed with such data will be output to a monitor 307, picture image photographing apparatus 308 and VTR 309. The superimposed data will be stored in a memorizing part 423 so as to be able to be output as required by such output apparatus 424 as, for example, a printer.

In case the radioactive ray detecting probe 312 and electronic scope 414 are to be used as combined, the intensity of the radioactive rays detected by the radioactive ray detecting apparatus 411 will be displayed in the display 416 together with the patient data and the like and, at the same time, the patient data and the like will be superimposed also on the endoscope image obtained by the electronic scope 414 when the input apparatus 422 is operated. This superimposed video signal will be delivered to the monitor 307, picture image photographing apparatus 308 and VTR 309 and the endoscope image displaying the radioactive ray intensity will be displayed on the picture surface. Further, this radioactive ray intensity will be stored in the memorizing part 423 together with the patient data. This memorizing part 423 can stored the data of each patient and can locate the accumulated data of each patient by operating the input apparatus 422.

Thus, according to this embodiment, the peculiarity to the resistor and the characteristic of the resistor with the cancer can be investigated while making the disposition of the data of each patient efficient.

The other formations are the same as in the 19th embodiment.

There is known a photo-dynamic therapy (abbreviated as PDT) wherein some kind of tumor affinable chemicals is administered and is excited by a laser light to generate a fluorescence to discover a tumor. As in FIG. 46, a laser light generated by a laser generating apparatus 432 may be fed to a radioactive ray detecting probe 431 to utilize the above mentioned photo-dynamic therapy.

In FIG. 46, the tip part of an elongated insertable part 433 provided on the radioactive ray detecting probe 431 and inserted into the body cavity is provided with a radioactive ray detecting sensor 351 and the exit end surface of a laser light guide fiber 434 formed of a fiber bundle. The laser light guide fiber 434 and a signal line 436 connected to the radioactive ray detecting sensor 351 are inserted through the insertable part 433 and are extended out of the insertable part 433 at the rear end. Then, the laser light guide fiber 434 is connected to a laser generating apparatus 432 and the signal line 436 is connected to a radioactive ray detector 313. This radioactive ray detector 313 is connected to the laser generating apparatus 432 so that, in case the intensity of the radioactive rays is higher than a preset intensity, a trigger signal will be output to the laser generating apparatus 432 to instruct the above mentioned laser generating apparatus 433 to generate a laser light.

The above mentioned radioactive ray detecting probe 431 will be excited by radiating a laser light and will be inserted into the body cavity after the fluorescence emitting chemicals is administered to detect radioactive rays emitted from the cancer 372. By the radioactive ray detector 313, the intensity of the radioactive rays will be measured and will be compared with a preset radioactive ray intensity and, in case the measured intensity is higher than this set intensity, a trigger signal will be output to the laser generating apparatus 432. When the trigger signal is input, a laser light will be generated by the laser generating apparatus and will radiate the cancer 372 from the exit end surface of the tip part of the insertable part 433 through the laser light guide fiber 434. The cancer 372 radiated with the laser light will generate a fluorescence so that the observer may sight the cancer 372 with an endoscope or the like (not illustrated).

Figure 47:
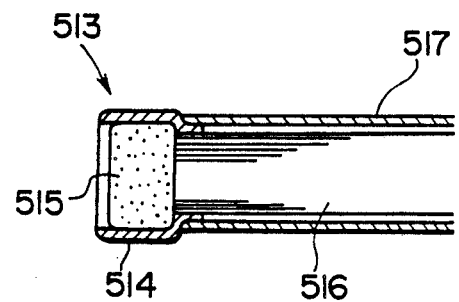
FIG. 47 is a sectioned view showing another example of a radioactive ray detecting probe inserted through a channel in the 19th and 20th embodiments.
Figure 48:
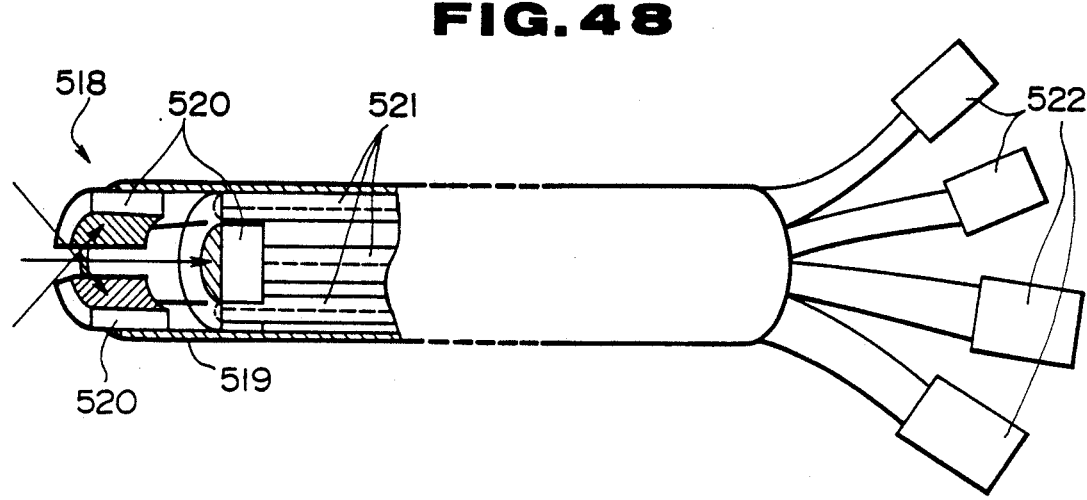
FIGS. 48 and 49 are partly sectioned perspective views each showing further another example of a radioactive ray detecting probe inserted through a channel in the 19th and 20th embodiments.
Figure 49:
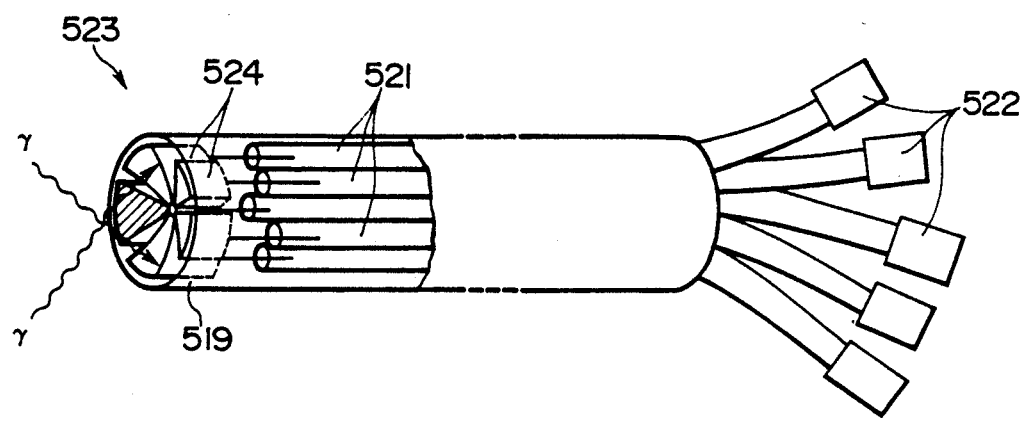

Other examples of radioactive ray detecting probes to be inserted through the channel 322, for example, in the 19th and 20th embodiments are shown in FIGS. 47 to 49.

In a probe 513 shown in FIG. 47, a scintillator 515 is internally provided within a cover 514 of the tip part and a light guide bundle 516 is located at the entrance end on the back surface of this scintillator 515 and is coated with a tube 517.

In a detecting probe 518 shown in FIG. 48, a plurality of detecting devices 520 are arranged in the center and on the inside surface of a cylindrical probe tip part 519 and are connected respectively to a plurality of coaxial lines 521. The way, the reference numeral 522 represents a connector. According to this probe, radioactive rays in other directions than the axial direction of the probe can be sensed by the detecting devices 520 provided on the inside surface of the cylinder and radioactive rays in the axial direction can be sensed by the detecting device 520 in the center of the cylinder.

In a detecting probe 523 shown in FIG. 49, a plurality of detecting devices 524 are arranged concavely and peripherally inside a cylindrical probe tip part 519. Therefore, the direction of radioactive rays can be sensed by the sensing positions of the respective detecting devices 524.

Figure 50:
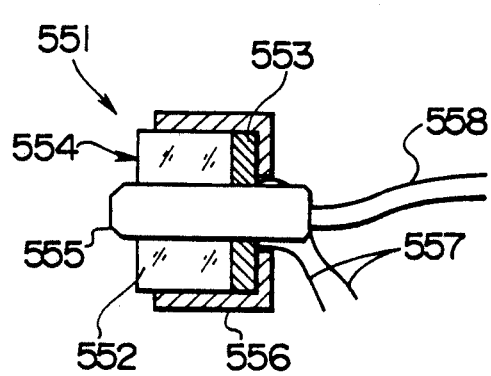
FIG. 50 is a sectioned view showing a radioactive ray detecting probe integrating a radioactive ray detecting device with a radiation temperature sensor.
Figure 51:
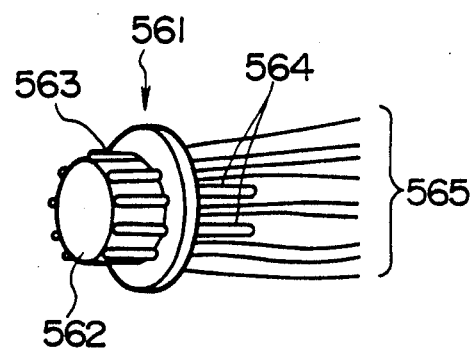
FIG. 51 is a sectioned view showing a radioactive ray detecting probe integrating a radioactive ray detecting device with a thermocouple.

Examples of a radioactive ray detecting probe wherein a radioactive ray detecting device is made integral with a temperature sensor are shown in FIGS. 50 and 51.

FIG. 50 is a sectioned view of a radiation temperature sensor and radioactive ray detecting device made integral with each other A temperature sensor fitted radioactive ray detector 551 shown in FIG. 50 is provided with a radiation temperature sensor 555 in the central part of a radioactive ray detector 554 consisting of a scintillator 552 and photodiode 553. The above mentioned radioactive ray detector 554 is covered on the outer peripheral surface and rear end surface with a radioactive ray shielding member 556. In the drawing, the reference numeral 557 represents a lead wire of the photodiode 553 and 508 represents a lead wire of the radiation temperature sensor 555.

FIG. 51 is a perspective view of thermocouples and a radioactive ray detecting device made integral with each other.

A temperature sensor fitted radioactive ray detector 561 shown in FIG. 51 is provided with a plurality of thermocouples 563 on the outer periphery of a columnar semiconductor radioactive ray detector 562. In the drawing, the reference numeral 564 represents a pin of the semiconductor radioactive ray detector 562 and 565 represents a lead wire of the thermocouple 563.

By using such temperature sensor fitted radioactive ray detector 551 or 561 in a hyperthermia, a tumor part can be sensed by the radioactive ray detector 554 or 562, the temperature of the tumor part can be measured by the temperature sensor 555 or thermocouples 563 and therefore the temperature of the tumor part can be accurately measured.

The temperature sensor to be made integral with the radioactive ray detector is not limited to be a radiation temperature sensor or thermocouple but may be a thermistor or IC temperature sensor.

Figure 52:
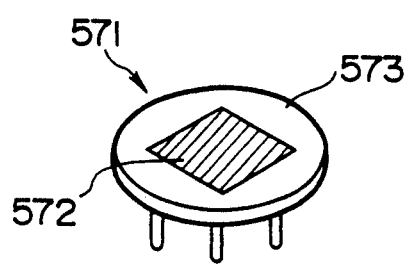
FIGS. 52 and 53 are perspective views of a semiconductor radioactive ray detector in which the package is made circular.
Figure 53:
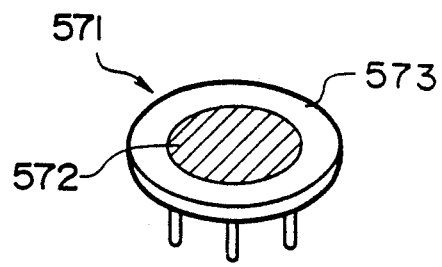

Also, as shown in FIG. 52, in the semiconductor radioactive ray detector 571, the contour of the package 573 of the semi-conductor 572 may be made circular. In a case, the shape of the aperture exposing the semi-conductor 572 may be rectangular as shown in FIG. 52 or circular as shown in FIG. 53.

Figure 54:
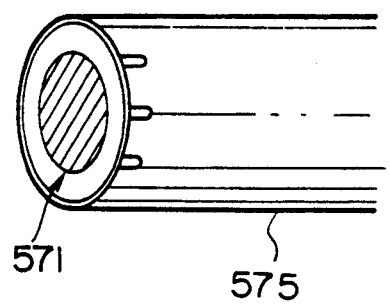
FIG. 54 is an explanatory view showing a semiconductor radioactive ray detector in which the package is made circular as fitted to the tip part of an endoscope.

Thus, when the package 573 of the semiconductor radioactive ray detector 571 is formed to be circular, as compared with the case that the package is rectangular, as shown in FIG. 54, the semiconductor radioactive ray detector 571 will be able to be more easily fitted to the tip part of the insertable part 575 of a side view or oblique view type endoscope or to the tip part of a probe or catheter.

Figure 55:
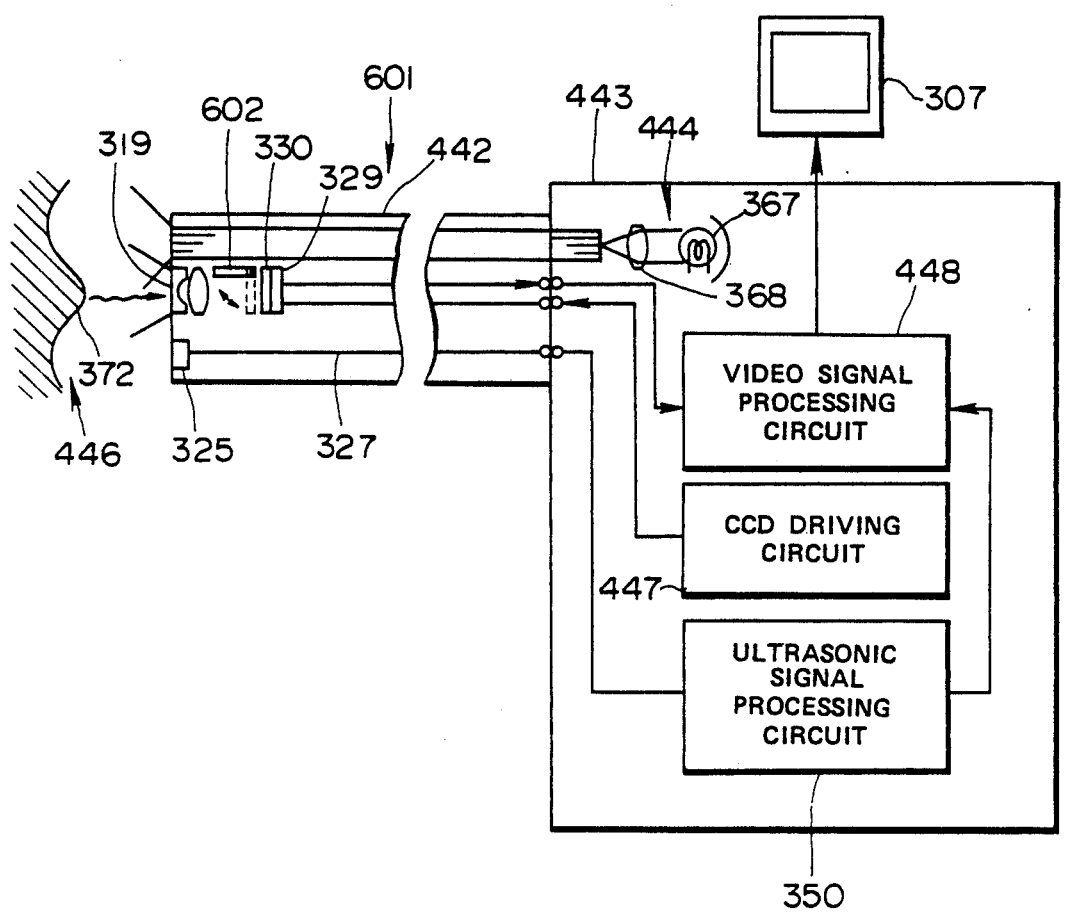
FIG. 55 is an explanatory view showing the formation of an endoscope apparatus in the 23rd embodiment of the present invention.

The 23rd embodiment of the present invention is shown in FIG. 55.

The same as in the 21st embodiment shown in FIG. 44, an endoscope 601 in this embodiment is an electronic endoscope having an ultrasonic probe 325 but is not provided with a radioactive ray detecting sensor 351, amplifier 451 and radioactive ray detecting circuit 449. In this embodiment, an imaging solid state imaging device as, for example, a CCD 329 is used simultaneously as a radioactive ray detecting means. That is to say, when radioactive rays as $\gamma$ rays enter the above mentioned CCD 329, these radioactive rays will contact a PN junction in the light receiving part of the CCD 329 and will issue a signal, a bright point will appear on a picture surface of a monitor 307 and the radioactive rays will be detected by this bright point.

Also, in this embodiment, a filter 602 attenuating radioactive rays and made of an optically transparent lead glass or the like is removably provided on the front surface of the CCD 329. Therefore, in an ordinary observation, when the above mentioned filter 602 is fitted to the front surface of the CCD 329, an image with which no bright point appears and which is easy to see will be able to be obtained on the picture surface of the monitor 307.

Thus, by detecting radioactive rays and imaging with one solid imaging device, the insertable part tip of the endoscope 601 can be made small.

The other formations, operations and effects are the same as in the 21st embodiment.

The present invention is not limited to the above mentioned respective embodiments. For example, in an ultrasonic endoscope provided with a solid state imaging device, the solid state imaging device, ultrasonic vibrator and radioactive ray detecting device may be made integral.

The color imaging system using a solid state imaging device may be of a simultaneous type provided with a color filter array on the front surface of a solid state imaging device or of a field sequential type sequentially switching the illuminating light to R. G and B, etc.

The radioactive rays are not limited to $\gamma$ rays but may be $\alpha$ and $\beta$ rays.

It is apparent that, in this invention, a wide range of different working modes can be formed on the basis of this invention without deviating from the spirit and scope of the invention. This invention is not restricted by its specific working modes except being limited by the appended claims.

What is claimed is:

1. A radioactive ray detecting endoscope comprising:
   an elongated insertable part having a tip part and a rear end;
   ultrasonic imaging means provided in the tip part of said insertable part and having a transmitting means for transmitting ultrasonic waves toward an observed part and receiving means for receiving echoes, from the observed part, of the ultrasonic waves emitted from said transmitting means, said ultrasonic imaging means for outputting a signal which forms an ultrasonic image of said observed part; and
   a radioactive ray detecting means arranged in the tip part of said insertable part for detecting radioactive rays.

2. A radioactive ray detecting endoscope according to claim 1 wherein said ultrasonic imaging means has an observing direction for observing said observed part and said radioactive ray detecting means has a detecting direction for detecting said radioactive rays, the observing direction and the detecting direction substantially coinciding with each other.

3. A radioactive ray detecting endoscope according to claim 2 wherein the observing direction of said ultrasonic imaging means and the detecting direction of said radioactive ray detecting means are intersecting directions of an axial direction of said insertable part.

4. A radioactive ray detecting endoscope according to claim 1 wherein the transmitting means and the receiving means of said ultrasonic imaging means are combined in a single ultrasonic vibrator.

5. A radioactive ray detecting endoscope according to claim 1 wherein said ultrasonic imaging means and said radioactive ray detecting means are integral with each other.

6. A radioactive ray detecting endoscope according to claim 5 wherein said ultrasonic imaging means and said radioactive ray detecting means are integrally rotatable.

7. A radioactive ray detecting endoscope according to claim 1 further comprising a first display means connected to said ultrasonic imaging means for displaying said ultrasonic image of the observed part based on the signal from said ultrasonic imaging means and a second display means connected to said radioactive ray detecting means for displaying radioactive ray information detected by said radioactive ray detecting means.

8. A radioactive ray detecting endoscope according to claim 7 wherein said first display means displaying said ultrasonic image and said second display means displaying the radioactive ray information are combined in a single display device.

9. A radioactive ray detecting endoscope according to claim 1 further comprising a treated tool channel provided within said insertable part.

10. A radioactive ray detecting endoscope according to claim 9 wherein said radioactive ray detecting means is inserted through said treating tool channel and arranged in said treating tool channel in said tip part of said insertable part.

11. A radioactive ray detecting endoscope according to claim 1 further comprising a collimator provided around said radioactive ray detecting means said collimator regulating a radioactive ray detecting direction.

12. A radioactive ray detecting endoscope according to claim 11 wherein said collimator is made of a radioactive ray attenuating material having at least one radioactive ray transmitting part in a predetermined direction.

13. A radioactive ray detecting endoscope according to claim 12 wherein said radioactive ray attenuating material is selected from the group consisting of lead, tungsten, stainless steel, lead glass, concrete, steel and mercury.

14. A radioactive ray detecting endoscope according to claim 1 wherein said radioactive ray detecting means is removably fitted to the tip part of said insertable part.

15. A radioactive ray detecting endoscope according to claim 1 wherein said radioactive ray detecting means has a plurality of radioactive ray detectors provided in the tip part of said insertable part.

16. A radioactive ray detecting endoscope according to claim 1 further comprising an observing window being provided in said tip part of said insertable part and an optical image observing means for observing an output optical image of said observed part by receiving light returnign from the observed part through said observing window.

17. A radioactive ray detecting endoscope according to claim 1 further comprising an illuminating window being provided in said tip part of said insertable part and an illuminating means for illuminating a visual field through said illuminating window.

18. A radioactive ray detecting endoscope according to claim 16 wherein said ultrasonic observing means has an ultrasonic observing direction, said radioactive ray detecting means has a detecting direction, said optical image observing means has an optical observing direction, said ultrasonic observing direction, said detecting direction and said optical observing direction substantially coincide with one another.

19. A radioactive ray detecting endoscope according to claim 18 wherein said ultrasonic observing direction, said detecting direction and said optical observing direction are intersecting directions of an axial direction of said insertable part.

20. A radioactive ray detecting endoscope according to claim 16 wherein said optical image observing means comprises an image forming optical system, an eyepiece part and an image transmitting means, said image forming optical system provided in the tip part of said insertable part for receiving said light returning from the object and for forming an object image, said eyepiece part provided on the rear end of said insertable part and said image transmitting means for transmitting to said eyepiece part the object image formed by said image forming optical system.

21. A radioactive ray detecting endoscope according to claim 16 wherein said optical image observing means comprise an image forming optical system for receiving said light returning from the object and for forming observed part image and said optical image observing means further comprises a solid state imaging device arranged in an image forming position of said image forming optical system.

22. A radioactive ray detecting endoscope according to claim 21 wherein said radioactive ray detecting means and said solid state imaging device are integral with each other.

23. A radioactive ray detecting endoscope according to claim 16 wherein said optical image observing means includes an optical imaging means for producing said output optical image and said radioactive ray detecting endoscope further comprises a first display means connected to said ultrasonic imaging means for displaying the ultrasonic image of the observed part base on the signal from said ultrasonic imaging means, a second display means connected to said radioactive ray detecting means for displaying information about the radioactive rays detected by said radioactive ray detecting means and a third display means connected to said optical imaging means for displaying the optical image with an optical image signal from said optical imaging means.

24. A radioactive ray detecting endoscope according to claim 23 wherein at least two of said first display means, said second display means and said third display means are combined into a single display device.

25. A radioactive ray detecting endoscope according to claim 1 wherein said transmitting means and said receiving means of said ultrasonic means are combined into a single ultrasonic probe.

* * * * *